United States Patent
Kusens et al.

(10) Patent No.: US 10,147,256 B2
(45) Date of Patent: Dec. 4, 2018

(54) ELECTRONIC IDENTIFICATION, LOCATION TRACKING, COMMUNICATION AND NOTIFICATION SYSTEM

(71) Applicant: COLLATERAL OPPORTUNITIES, LLC, Wilmington, DE (US)

(72) Inventors: Bruce Howard Kusens, North Miami Beach, FL (US); Michael Kusens, Cooper City, FL (US); Arthur Miller, Las Vegas, NV (US)

(73) Assignee: COLLATERAL OPPORTUNITIES, LLC, Wilmington, DE (US)

( * ) Notice: Subject to any disclaimer, the term of this patent is extended or adjusted under 35 U.S.C. 154(b) by 0 days.

(21) Appl. No.: 15/934,965

(22) Filed: Mar. 24, 2018

(65) Prior Publication Data
US 2018/0247476 A1 Aug. 30, 2018

Related U.S. Application Data

(63) Continuation-in-part of application No. 15/818,020, filed on Nov. 20, 2017, now Pat. No. 9,997,001, (Continued)

(51) Int. Cl.
*G07C 9/00* (2006.01)
*H04W 4/02* (2018.01)
(Continued)

(52) U.S. Cl.
CPC ... *G07C 9/00309* (2013.01); *G06F 17/30867* (2013.01); *G07C 9/00103* (2013.01);
(Continued)

(58) Field of Classification Search
CPC ...... G07C 9/00309; G07C 2009/00769; G07C 9/00111; G07C 9/00007; G07C 9/00571; G07C 2009/00793; G07C 2209/63
(Continued)

(56) References Cited

U.S. PATENT DOCUMENTS 5,642,303 A 6/1997 Small
6,812,824 B1 11/2004 Goldinger
(Continued)

FOREIGN PATENT DOCUMENTS

KR 20120031787 A 4/2012
WO 2010046727 A2 4/2010

OTHER PUBLICATIONS

International Search Report for PCT/US2015/052486 dated Jan. 28, 2016.
(Continued)

*Primary Examiner* — Mark Blouin
(74) *Attorney, Agent, or Firm* — Daniel S. Polley, P.A.

(57) ABSTRACT

A method and system in a first embodiment that allows authorized individuals access into controlled access locations and the ability to grant temporary and limited access to guests into these locations. The method and system allow for navigational services to be provided to members and guests, and real-time tracking and confirmation to members and administrators that guests have arrived at their destination and did not enter any unauthorized areas. The method preferably can work through a system of wireless radio, sound and/or light-based beacons communicating with member and guest's electronic devices. Members and administrators can send one or more temporary electronic access keys to a guest's smartphone or other electronic device. Wireless radio, sound and/or light-based beacons provide an access control and location tracking system with real-time data about the member and guest whereabouts, allowing for the confirmation and tracking. A system and method in a second embodiment for identifying a customer's location within a facility or place of business, such as, but not limited to a casino. The system and method provide notification to company representatives upon arrival of the customer at the given location. Additionally, the method and (Continued)

system allow for navigational services to be provided to customers, and real-time location determination, location tracking and confirmation to customers of location and rewards program status. The disclosed method and system can work through a system of wireless radio, sound and/or light-based beacons communicating with the customer's smartphone, computer system, or other electronic device.

28 Claims, 15 Drawing Sheets

Related U.S. Application Data which is a continuation of application No. 15/627,820, filed on Jun. 20, 2017, now Pat. No. 9,858,741, which is a continuation of application No. 15/286,753, filed on Oct. 6, 2016, now Pat. No. 9,691,206, which is a continuation of application No. 15/055,477, filed on Feb. 26, 2016, now Pat. No. 9,466,163, which is a continuation-in-part of application No. 14/827,222, filed on Aug. 14, 2015, now Pat. No. 9,424,699.

(60) Provisional application No. 62/037,684, filed on Aug. 15, 2014.

(51) Int. Cl.
*H04W 64/00* (2009.01)
*G06F 17/30* (2006.01)

(52) U.S. Cl.
CPC ...... *G07C 9/00111* (2013.01); *G07C 9/00571* (2013.01); *G07C 9/00817* (2013.01); *H04W 4/02* (2013.01); *H04W 64/00* (2013.01); *G07C 2009/00388* (2013.01); *G07C 2009/00769* (2013.01); *G07C 2209/02* (2013.01)

(58) Field of Classification Search
USPC ....................................................... 340/5.61
See application file for complete search history.

(56) References Cited

U.S. PATENT DOCUMENTS

| | | | |
|---|---|---|---|
| 7,367,497 B1 | 5/2008 | Hill | |
| 7,600,679 B2 * | 10/2009 | Kshirsagar | G07C 9/00111 |
| | | | 235/375 |
| 8,009,013 B1 | 8/2011 | Hirschfeld | |
| 8,446,249 B2 * | 5/2013 | Gerstenkorn | G08C 19/00 |
| | | | 340/5.2 |
| 9,100,766 B2 | 8/2015 | Soulodre | |
| 9,838,849 B2 | 12/2017 | Kusens | |
| 2002/0030600 A1 | 3/2002 | Starner | |
| 2003/0146835 A1 | 8/2003 | Carter | |
| 2005/0136845 A1 | 6/2005 | Masuoka | |
| 2008/0109317 A1 | 5/2008 | Singh | |
| 2008/0144864 A1 | 6/2008 | Huon | |
| 2012/0154115 A1 | 6/2012 | Herrala | |
| 2013/0115969 A1 | 5/2013 | Holmes | |
| 2013/0229263 A1 | 9/2013 | Graczyk | |
| 2014/0287778 A1 | 9/2014 | Jones et al. | |
| 2014/0379529 A1 | 12/2014 | Agasti | |
| 2016/0049028 A1 | 2/2016 | Kusens et al. | |
| 2016/0098676 A1 | 4/2016 | Kusens et al. | |
| 2016/0247342 A1 | 8/2016 | Kusens et al. | |
| 2017/0111770 A1 | 4/2017 | Kusens | |
| 2018/0084390 A1 | 3/2018 | Kusens | |

OTHER PUBLICATIONS

Applicant Collateral Opportunities, LLC's pending U.S. Appl. No. 14/866,756.
Applicant Collateral Opportunities, LLC's pending U.S. Appl. No. 15/802,594 (currently unpublished).
Applicant Collateral Opportunities, LLC's pending U.S. Appl. No. 15/825,752.
Applicant Collateral Opportunities, LLC's pending U.S. Appl. No. 15/897,114 (currently unpublished).
Applicant Collateral Opportunities, LLC's pending U.S. Appl. No. 15/845,417 (currently unpublished).

* cited by examiner

FIGURE 1: Registration of Member Device
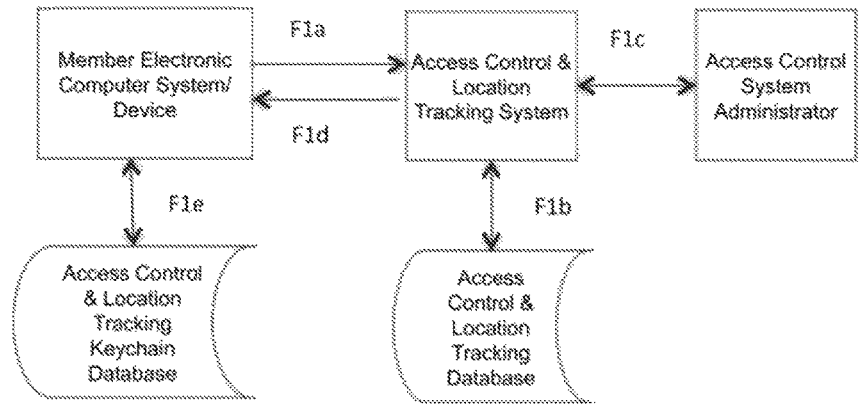
FIGURE 2: Sending Access Key to Guest Device
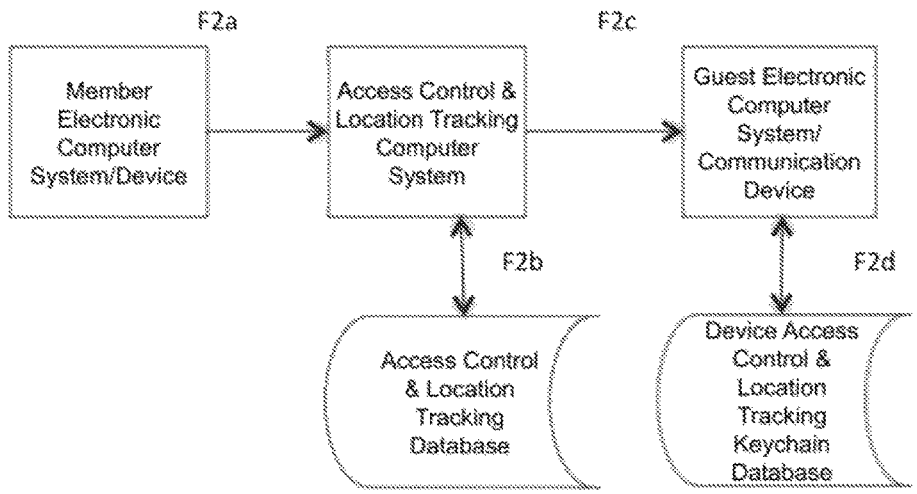

FIGURE 3: Determination of Access Rights
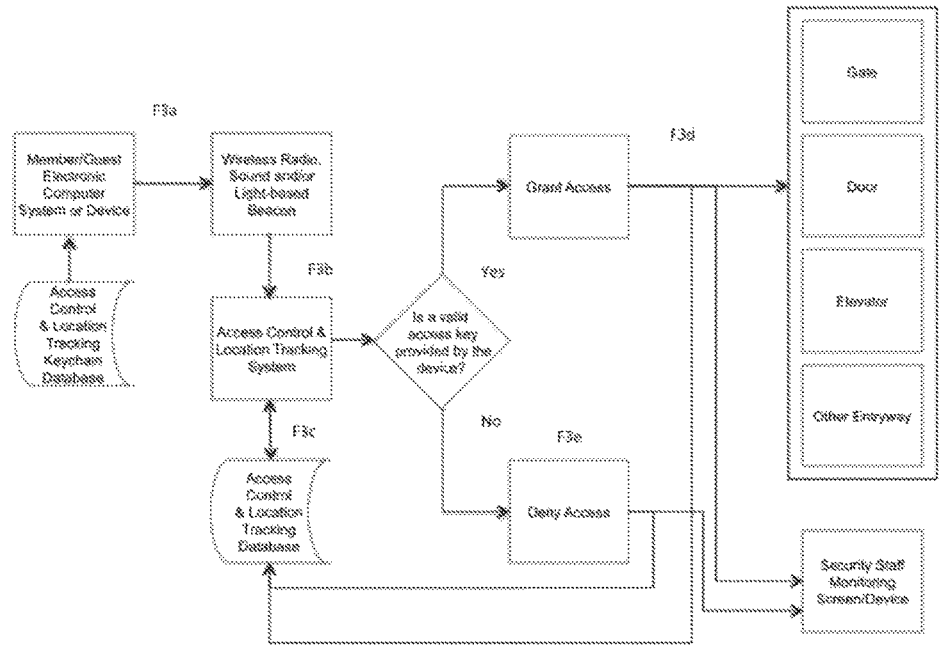
FIGURE 4: Determination of Authorized Location(s)
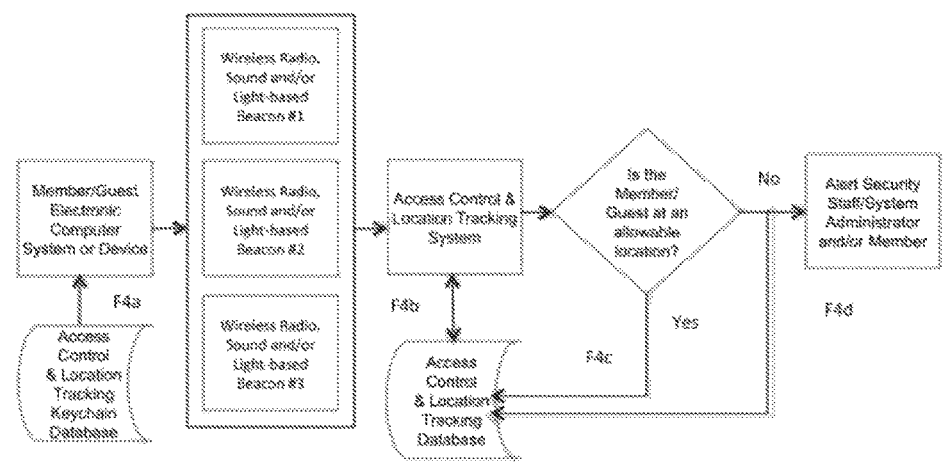

FIGURE 5: Determination of Arrival at Authorized Location(s)
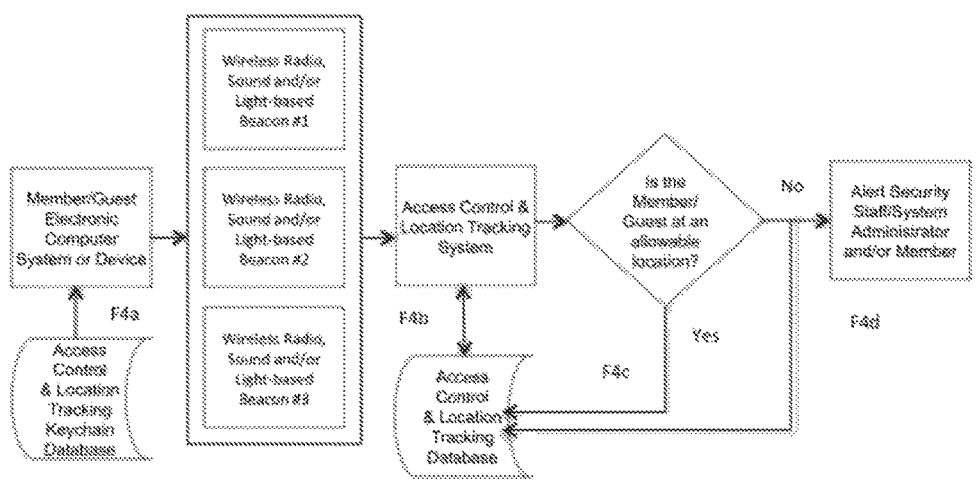
FIGURE 6: Determination of Location and Navigational Support
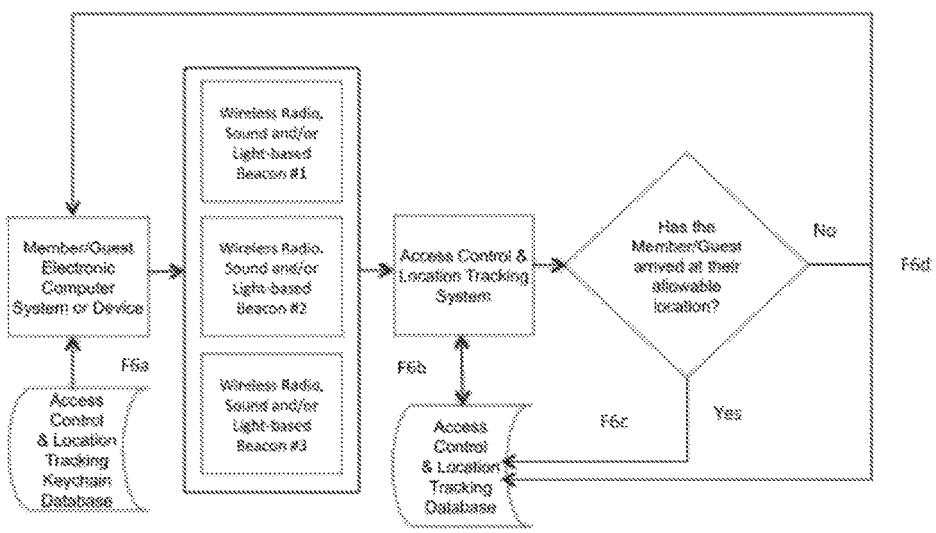

FIGURE 7: Access Control & Notification Rules Engine
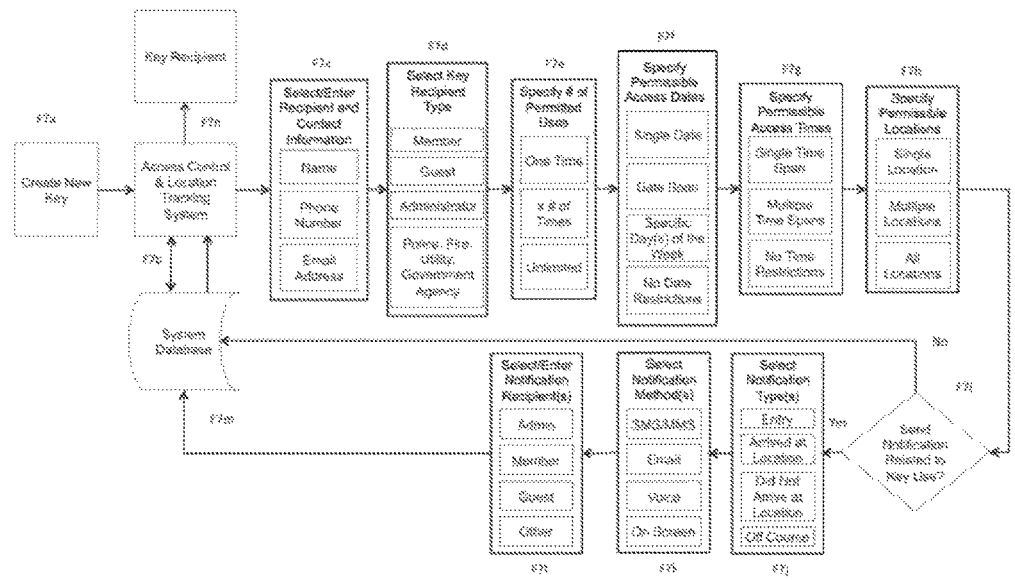
FIGURE 8: Storage of Keys in Keychain Database
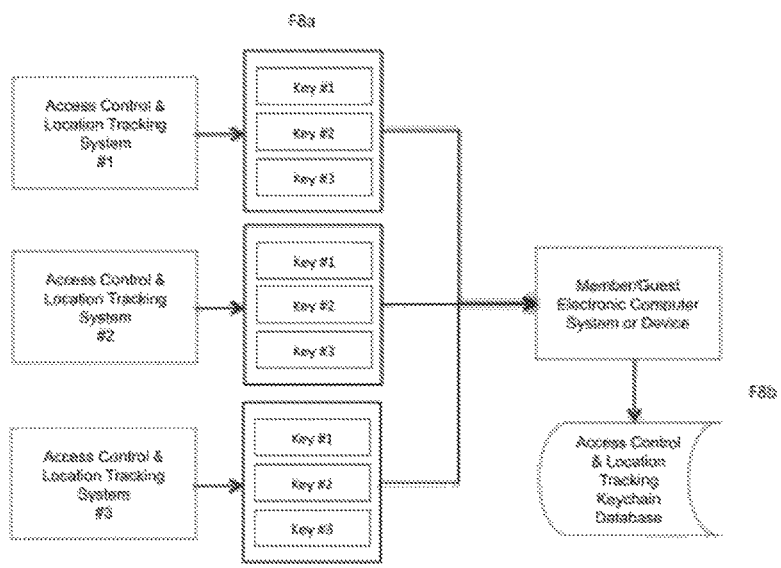

FIGURE 9: Manually Sending Keys from Device to Access Control & Location Tracking System
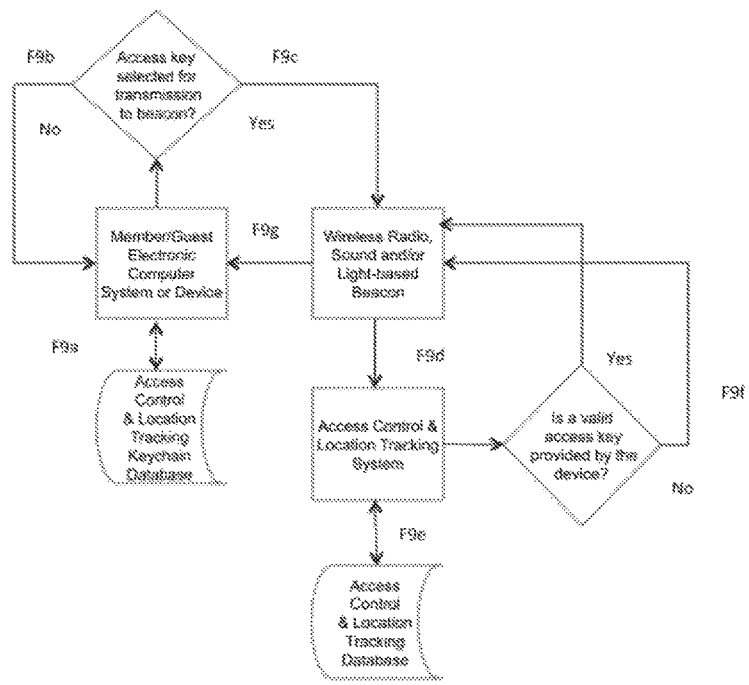

FIGURE 10: Auto-Prompting to Select a Key and Manual Key Selection to Send from Device to Access Control & Location Tracking System
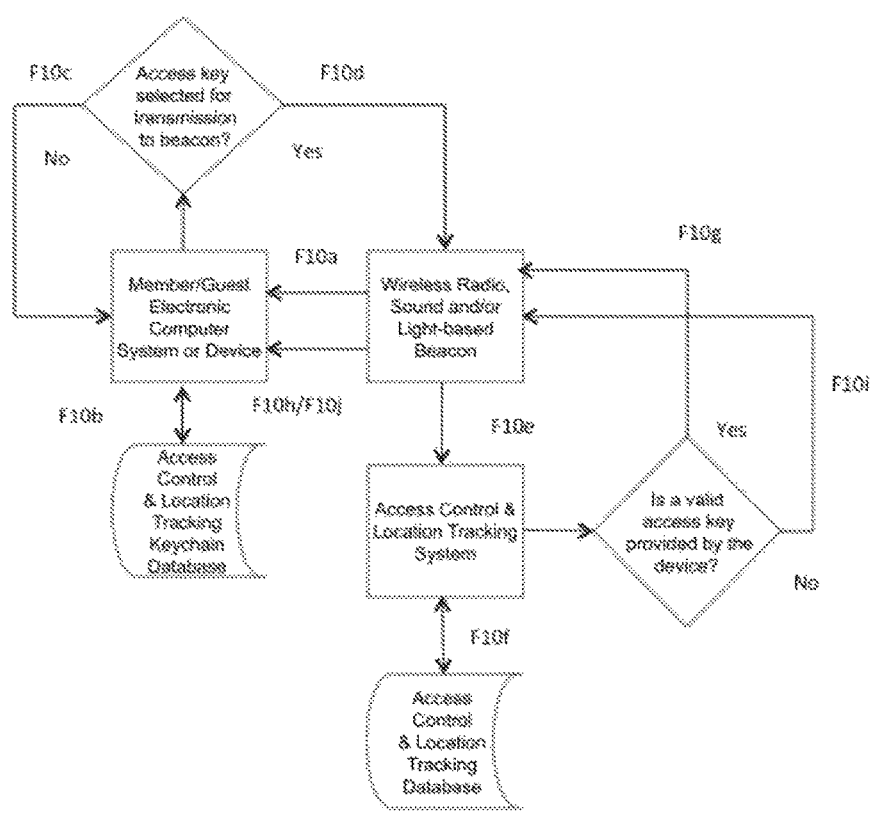

FIGURE 11: Auto-Prompting & Key Selection to Send from Device to Access Control & Location Tracking System
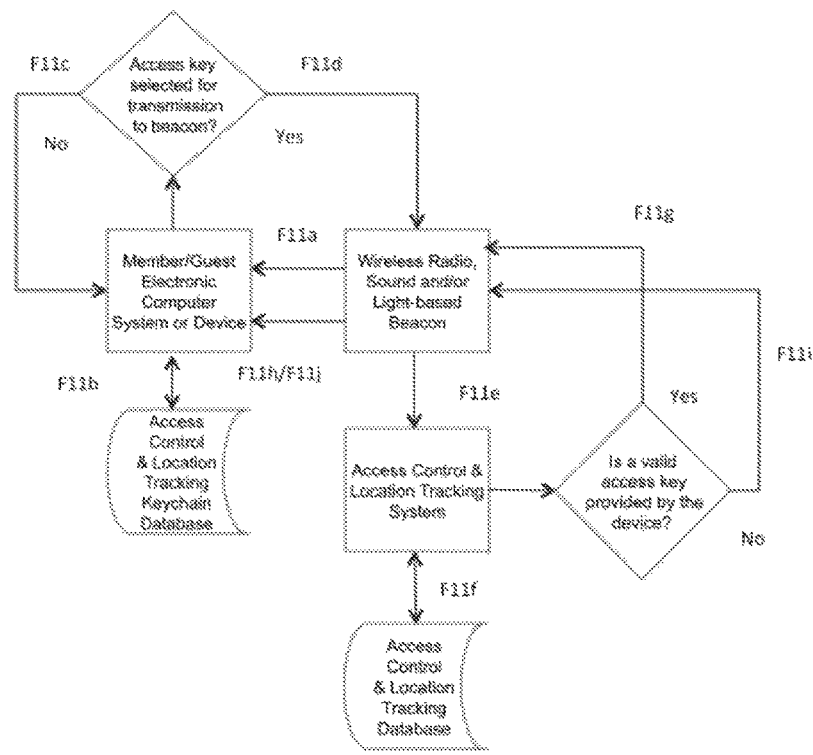
FIGURE 12: Process for a Guest to Request a Key from a Member
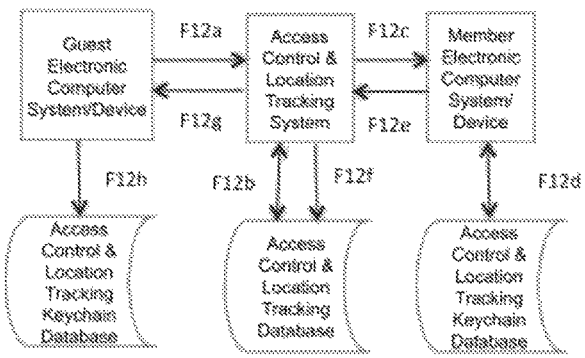

FIGURE 15: Registration of Customer's Device
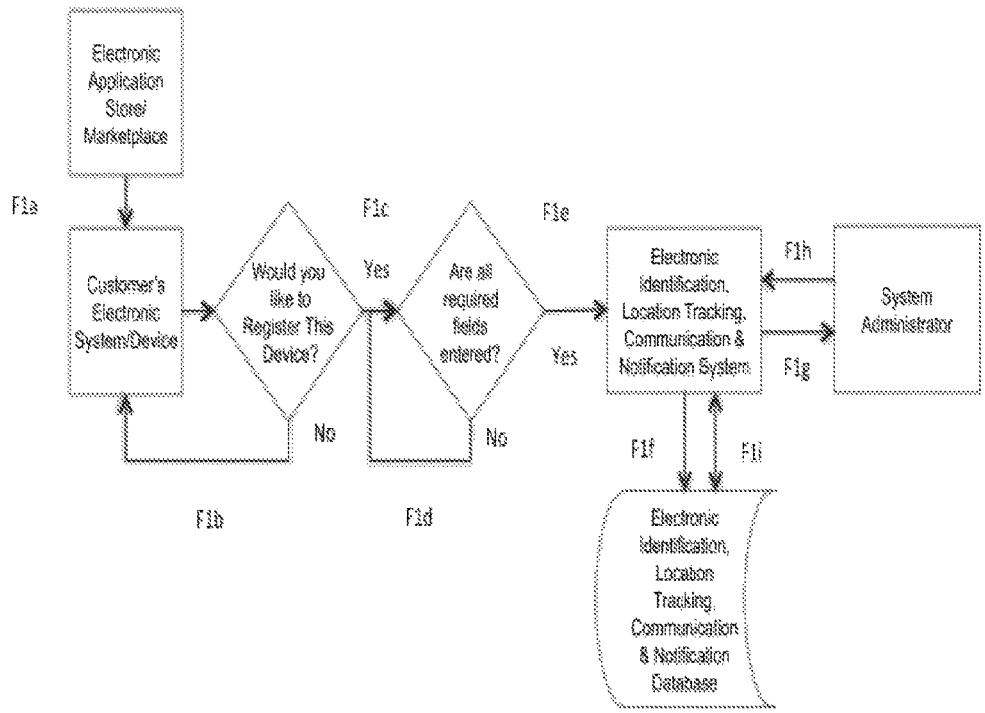
FIGURE 16: Registering a Beacon Location
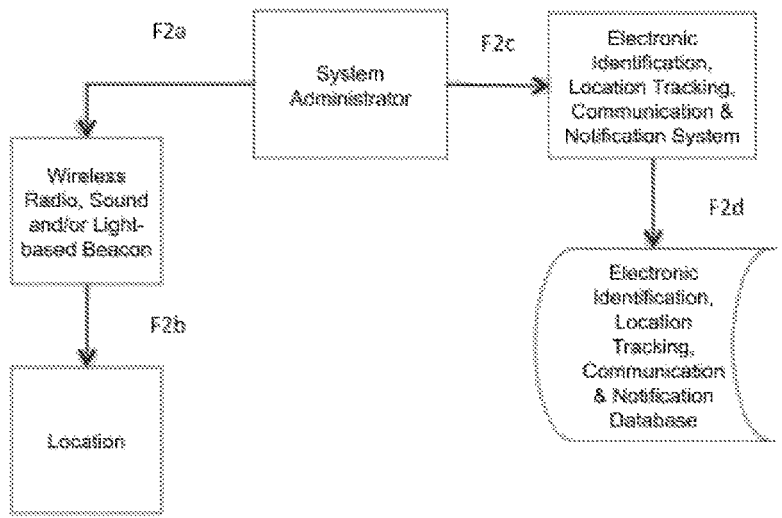

FIGURE 17: Determination of Presence at Location – Embodiment A
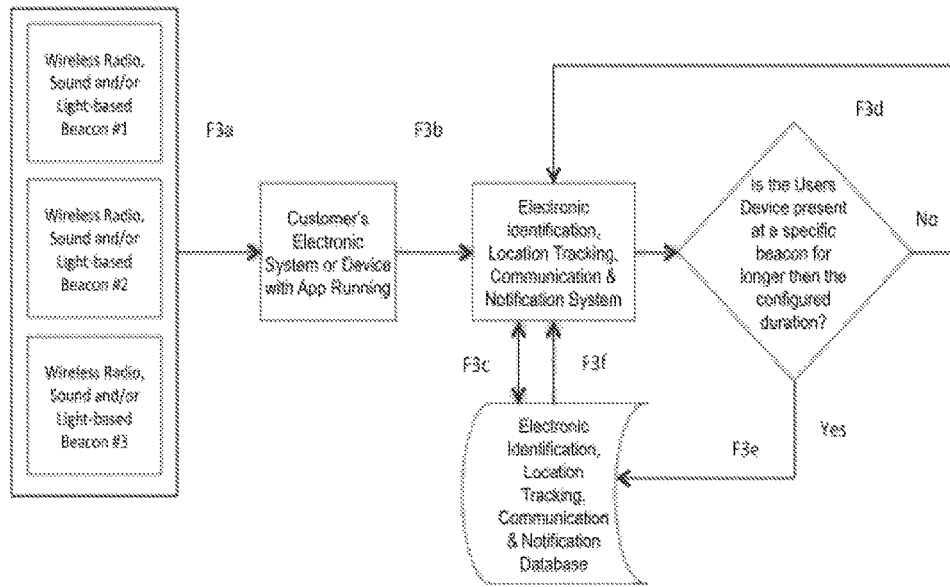
FIGURE 18: Determination of Presence at Location – Embodiment B
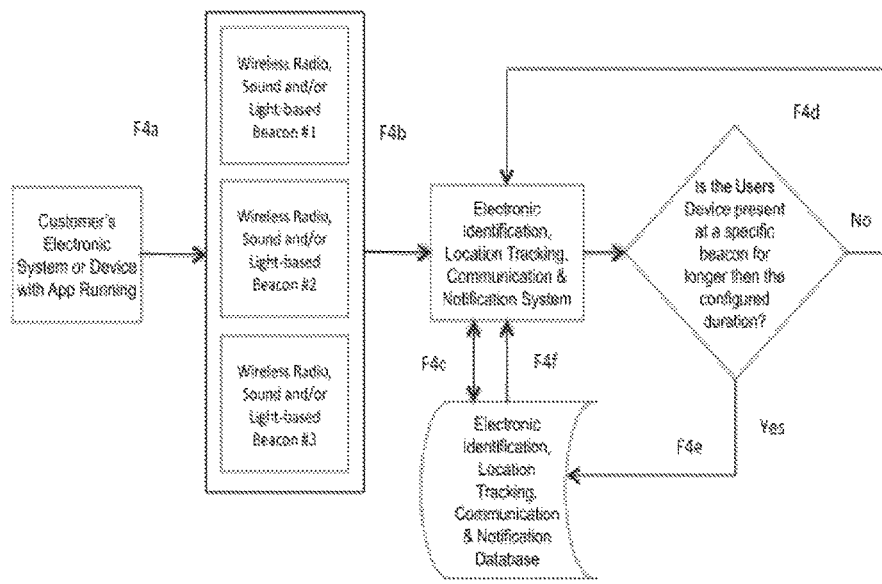

FIGURE 19: Notification Rules Engine
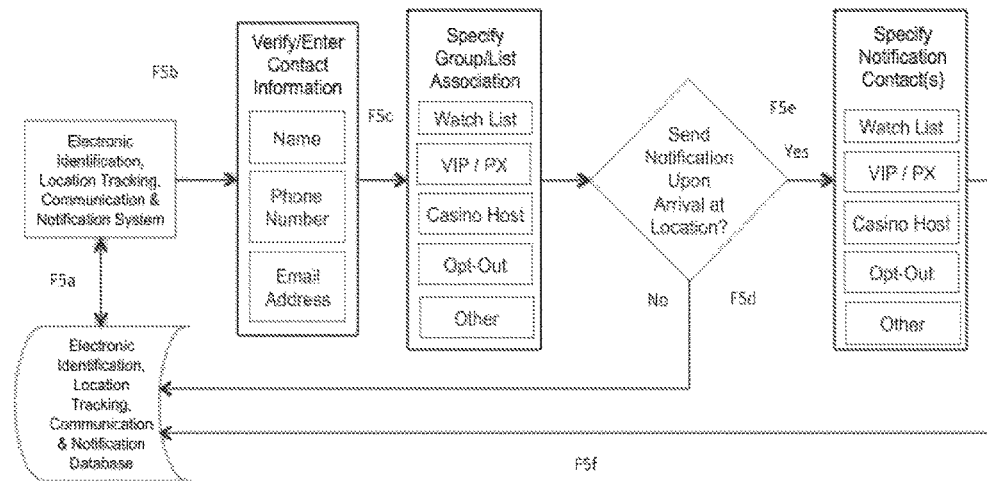
FIGURE 20: Determination and Delivery of Notifications
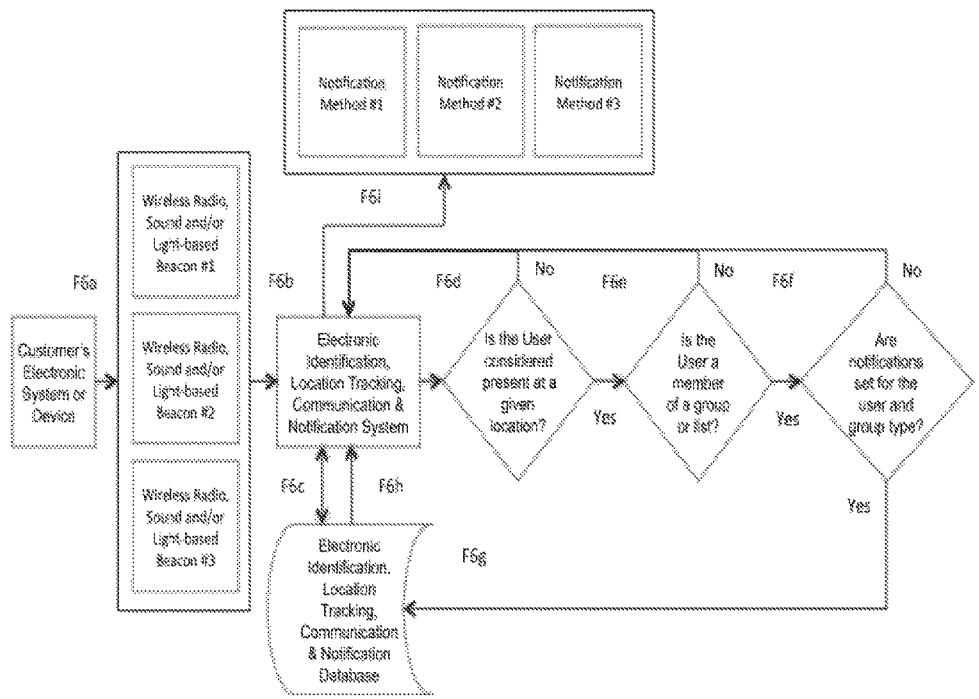

FIGURE 21: Determination and Delivery of Notifications – Embodiment B
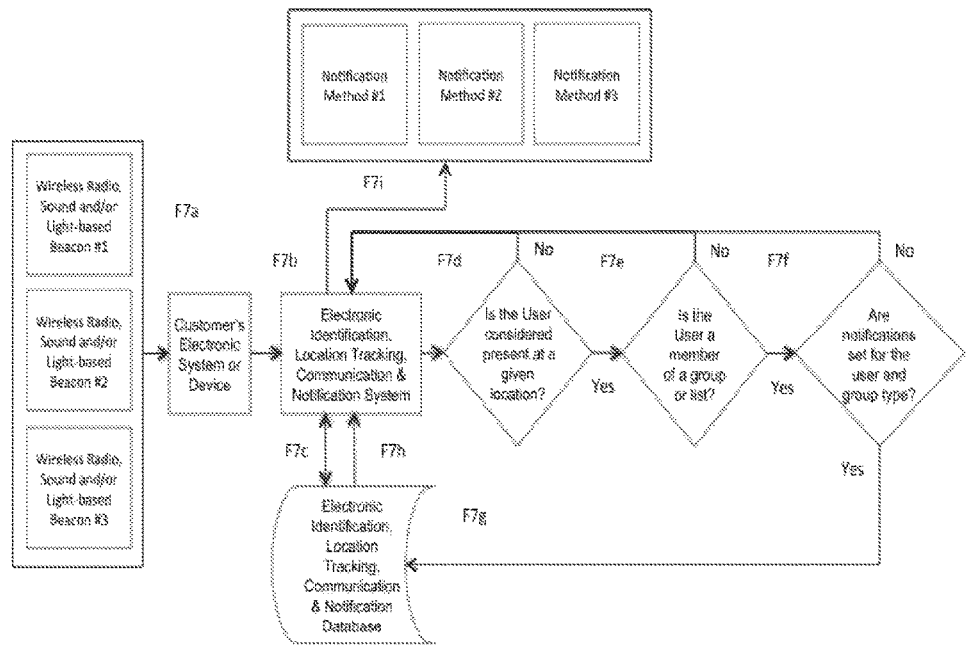
FIGURE 22: Presence Determination at a Location Rules Engine
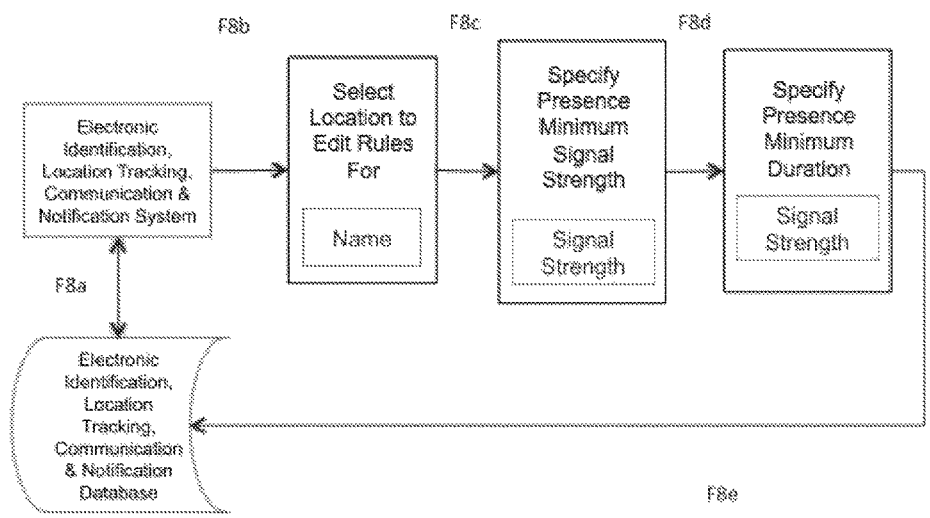

FIGURE 23: Process to Order Goods and/or Services from App
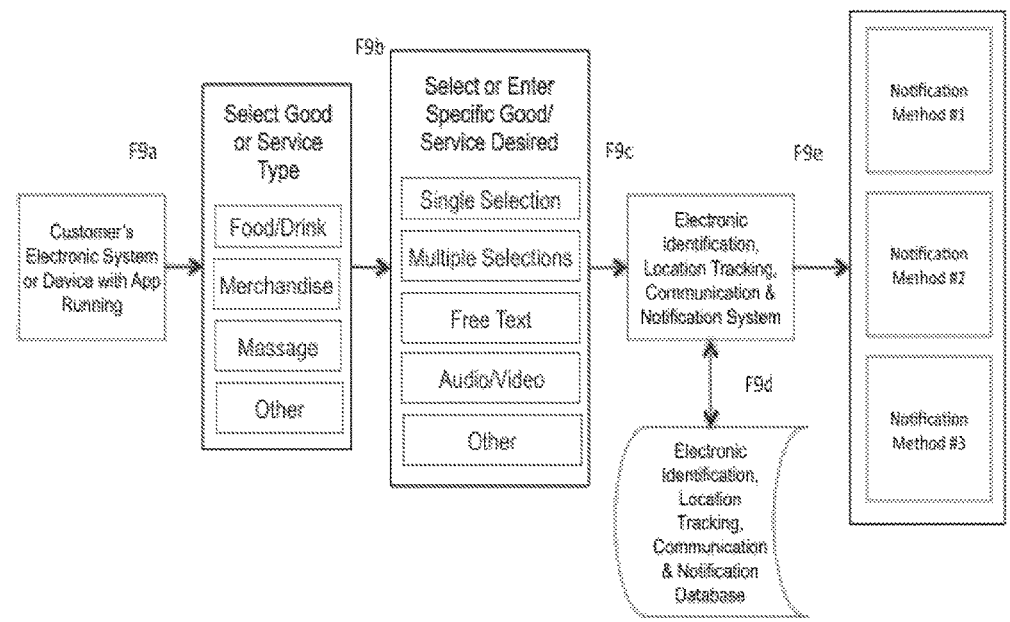
FIGURE 24: Delivery of Good and/or Services to Customers Current Location
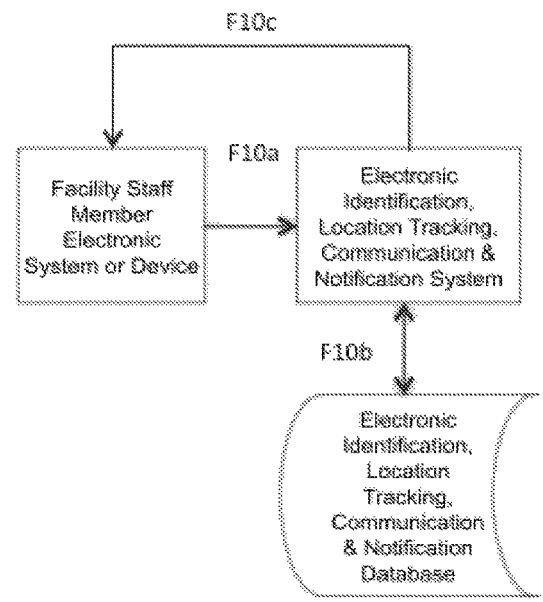

FIGURE 25: Customer Opt-Out of Rating/Monitoring by Facility
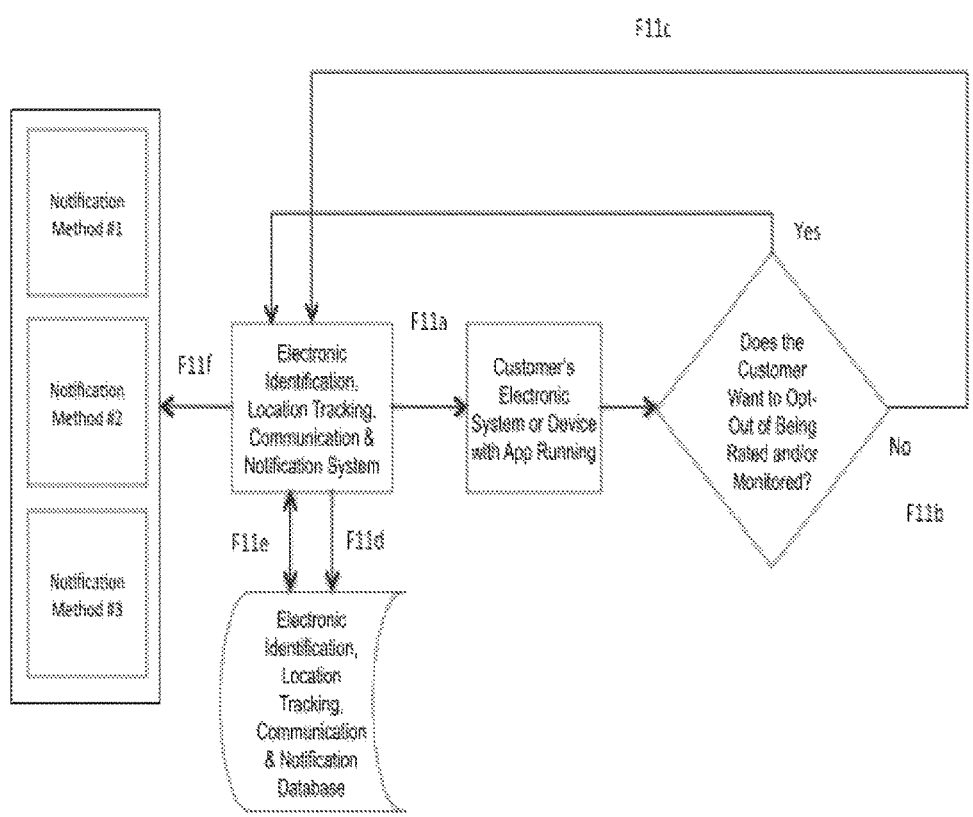

ELECTRONIC IDENTIFICATION, LOCATION TRACKING, COMMUNICATION AND NOTIFICATION SYSTEM This application is a continuation-in-part of U.S. application Ser. No. 15/818,020, filed Nov. 20, 2017, which is a continuation of U.S. application Ser. No. 15/627,820, filed Jun. 20, 2017, now U.S. Pat. No. 9,858,741, which is a continuation of U.S. application Ser. No. 15/286,753, filed Oct. 6, 2016, now U.S. Pat. No. 9,691,206, which is a continuation of U.S. application Ser. No. 15/055,477, filed Feb. 26, 2016, now U.S. Pat. No. 9,466,163, which is a continuation-in-part of U.S. application Ser. No. 14/827,222, filed Aug. 14, 2015, now U.S. Pat. No. 9,424,699, which claims priority to and the benefit of U.S. Application Ser. No. 62/037,684, filed Aug. 15, 2014. All of the above-identified applications are incorporated by reference in their entireties for all purposes.

BACKGROUND

Controlled access areas have become increasingly commonplace in modern society. From hospitals to gated communities, sensitive industries to prison complexes, there is a need to control the flow of human capital. Systems for doing so are often rudimentary, such as those that utilize a guard who checks an individual's identification and access rights. Other systems involve physical keycards and passes, which allow access past static checkpoints.

These systems are often insufficient for controlling and tracking the movement of guests who have access for a particular, limited purpose. Once past a static checkpoint, control systems have limited means for tracking a guest's movements. Furthermore, guests may become lost or enter into areas beyond the scope of their invitation.

The hospitality industry is highly competitive with companies always looking for competitive advantages, whether it be on price, features or customer service. In recent years, in an effort to differentiate themselves from other competitors, many hospitality companies such as Hotels, Restaurants and Casinos have implemented customer reward and tracking programs. These programs reward customers for a variety of reasons including, but not limited to, spending time at specific locations, spending money at specific locations and performing certain activities. Additionally, the reward programs provide a treasure trove of data for the companies on their customers, which assist in marketing efforts, administrative decisions and more.

Current systems require both the customer and company to proactively perform a manual task in order to be recognized at the location and receive the proper rewards program recognition. Most of the time this is done by the customer handing a card to a company representative and that card information then entered into an existing system. This process is often insufficient for proper tracking of the customer, time consuming and dependent on the customer physically remembering to hand the card to the company representative.

It is to addressing or reducing these problems that the current disclosure is directed.

SUMMARY OF THE DISCLOSURE

A method and system are described that allows members (as defined below), system administrators or other authorized individuals access into to controlled access locations; as well as the ability for members and administrators to grant temporary and limited access to guests into these locations. Additionally, the method and system allows for navigational services to be provided to members and guests, and real-time tracking and confirmation to members and administrators that guests have arrived at their destination and did not enter any unauthorized areas.

The disclosed method preferably can work through a system of wireless radio, sound and/or light-based beacons communicating with member and guest's smartphones, computer systems, or other electronic devices. Members and administrators can send one or more temporary electronic access keys to a guest's smartphone or other electronic device. Wireless radio, sound and/or light-based beacons provide an access control & location tracking system with real-time data about the member and guest whereabouts, allowing for the confirmation and tracking described above and below. Depending on the type of location using the system, in certain circumstances one or more members, in addition to guests, also may not have access to all restricted areas at the given location. As a non-limiting example, where the system is used by a condominium ("condo") building and a particular condo owner is delinquent on their Condo Association fees, access to community areas (i.e. exercise rooms, club house, etc.) for the particular condo owner could be restricted, but not the entrance, elevators or garage. As another non-limiting example, commercial buildings may allow a tenant to access the building entrance, elevator for their particular floor and garage, but not other floors of the building.

Additionally, a method is described that allows companies (as defined below), to identify a customer's location and provide notification to one or more company representatives upon arrival of the customer at a given location. Additionally, the method allows for navigational services to be provided to customers, and real-time location determination, location tracking and confirmation to customers of location and rewards program status.

The disclosed method preferably can work through a system of wireless radio, sound and/or light-based beacons communicating with the customer's smartphone, computer system, or other electronic device. Wireless radio, sound and/or light-based beacons provide a system with real-time data about the customer's whereabouts, allowing for the automated confirmation and tracking described above and below. Depending on the type of location using the system, in certain circumstances one or more functions of the system may not be available to customers and companies alike. As a non-limiting example, where the system is used by a company that provides food and beverage services, a customer can place an order for food/beverages and the order delivered to the person at their current location as determined by the system. As another non-limiting example, a company may choose to implement the notification system to have staff members notified of the arrival of a customer who is assigned to a specific group or list within the system.

The following definitions are provided for a better understanding of the disclosure:

| | |
|---|---|
| Access Control & Location Tracking Database | The electronic database where permissions and locations of guests and members are managed and stored. |

| | |
|---|---|
| Access Control & Location Tracking System | The specially programmed computer/electronic system which monitors guest and member authorizations and locations based on information received from and being in communication with wireless Radio, Sound and/or Light-based Beacons to monitor activity in controlled access areas. |
| Member/Guest Electronic Computer System or Device | A specially programmed computer system or electronic device including, but not limited to, cell phone, smartphone, key card, tablet, laptop or other computer system belonging to a member, guest, administrator or public service personnel. |
| Access Control & Location Tracking Keychain Database | An electronic database that stores digital access keys sent to a specific member, guest, administrator or public service personnel's device. The keychain database can store digital keys from one or more different access control & location tracking systems and is preferably stored on the member/guest's electronic device which stores the particular member's or guest's keys. This allows the system to be used at multiple locations via a single electronic device app. The other above defined database (Access Control & Location Tracking Database) is preferably provided at each location of installation for the system and stores the keys, member/guest information and access rights for the particular installation of the system. |
| Administrator | One or more persons responsible for the determining who is authorized to enter into a controlled access area. Alternatively or additionally, one or more persons responsible for entering, reviewing, overseeing, managing and/or maintaining information about each customer in the system as well as configuring location, notifications and group/list management. |
| Authorized Persons | Persons who have permission to enter a controlled access area. |
| Wireless Radio, Sound and/or Light-based Beacon | A small receiver/transmitter capable of operating on short and/or long range wireless communication between electronic devices. Capabilities include but are not limited to pinpointing its own location, utilizing or being programmed or designed to utilize the software in a smart phone, cellular phone or other electronic device to determine that device's location and bi-directional data transmission. Wireless radio, sound and/or light-based beacons can utilize technologies including, but not limited to, Near Field Communication (NFC), Bluetooth, WiFi, Light-Fidelity (LiFi), Ultrasound, InfraRed (IR), and Radio Frequency (RF). All of these technologies and similar current or similar later developed communication technologies are included in the term "wireless radio" wherever that term appears in this disclosure. |
| Checkpoint | A pre-determined location within a controlled access area where the Access Control & Location Tracking system is programmed to determine whether a member or guest has the necessary credentials to proceed further. |
| Controlled Access Area Or Controlled Access Location | Locations where the general public may not enter without permission from a member or administrator. (e.g. sensitive areas in hospitals, gated communities, prisons, private areas of businesses, apartment buildings). |
| Device | A smartphone, cellular phone, computer, tablet, laptop or any electronic device with wireless radio, sound and/or Light-based Beacon capability and specifically programmed with the below defined "Permissions Application". |
| Guest | An individual with temporary, limited access into all or part of a controlled access area. |
| Key | An electronic or digital code, which is stored in the permissions application. This code is checked against the access control & location tracking database to determine whether a member or guest has permission to be in a controlled access area at a given date and time. |
| Member | An individual with permission to be in a controlled access location, and authority to grant guests access to a controlled access location. |
| Permissions Application | A software based application which retains the permissions for entry into controlled access locations. This application can be run on a smartphone, computer, tablet, or other electronic device. |
| Electronic Identification, Location Tracking, Communication & Notification System Database | An electronic database where permissions and locations of guests and members are managed and stored. |
| Electronic Identification, Location Tracking, Communication & Notification System | A specially programmed system which monitors guest and member authorizations and locations based on information received from and being in communication with wireless radio, sound and/or light-based beacons which can be specifically positioned or placed in specific locations to monitor activity in controlled access areas. |
| Electronic Identification, Location Tracking, Communication & | A specially designed software application "App" that is installed on the customer's electronic system or device and which allows and directs the customer's electronic system or device to communicate with wireless radio, sound and/or light-based beacons in order to |

| | |
|---|---|
| Notification App | identify the customer's current location. |
| Customer | One or more persons who have entered the physical location of a company and/or are patrons of the company's business. |
| Facility Staffs Electronic System or Device | A computer system or device including, but not limited to, cell phone, smartphone, key card, tablet, laptop or other computer system belonging to a facility that is specially programmed and loaded with the Electronic Identification, Location Tracking, Communication & Notification Application or specially programmed to directly access and communicate with the Electronic Identification, Location Tracking, Communication & Notification System. |
| Customer's Electronic System or Device | A computer system or device including but not limited to cell phone, smartphone, key card, tablet, laptop or other computer system or electronic device belonging to a customer that is specially programmed with the Electronic Identification, Location Tracking, Communication & Notification App to permit communication with one or more wireless radio, sound and/or light-based beacons. |

BRIEF DESCRIPTION OF THE DRAWINGS

FIG. 1 is a block diagram of certain non-limiting components of the disclosed access control and location tracking system and also illustrating the steps/communications generally involved in the registration of a member device;

FIG. 2 is a block diagram of certain non-limiting components of the access control and location tracking system and also illustrating the steps/communications generally involved in sending an access key to a guest device;

FIG. 3 is a block diagram of certain non-limiting components of the access control and location tracking system and also illustrating the steps/communications generally involved in determining access rights;

FIG. 4 is a block diagram of certain non-limiting components of the access control and location tracking system and also illustrating the steps/communications generally involved in determining authorized locations;

FIG. 5 is a block diagram of certain non-limiting components of the access control and location tracking system and also illustrating the steps/communications generally involved in determining arrival at authorized locations;

FIG. 6 is a block diagram of certain non-limiting components of the access control and location tracking system and also illustrating the steps/communications generally involved in determining location and navigational support;

FIG. 7 is a block diagram and process flow for access control and the notification rules engines for the disclosed access control and location tracking system;

FIG. 8 is block diagram and process flow for the storage of electronic keys in the keychain database in connection with the disclosed access control and location tracking system;

FIG. 9 is a block diagram of certain non-limiting components of the access control and location tracking system and also illustrating the steps/communications generally involved in sending electronic keys from an electronic device to the access control and location tracking system;

FIG. 10 is a block diagram of certain non-limiting components of the access control and location tracking system and also illustrating the steps/communications generally involved in auto-prompting for selecting an electronic key for sending from an electronic device to the access control and location tracking system;

FIG. 11 is a block diagram of certain non-limiting components of the access control and location tracking system and also illustrating the steps/communications generally involved in auto-prompting and electronic key selection for sending from an electronic device to the access control and location tracking system;

FIG. 12 is a block diagram of certain non-limiting components of the access control and location tracking system and also illustrating the steps/communications generally involved in a guest requesting an electronic key from a member in connection with the access control and location tracking system;

FIG. 15 is a block diagram of certain non-limiting components of the disclosed electronic identification, location tracking, communication and notification system and also illustrating the steps/communications generally involved in the registration of a customer's device;

FIG. 16 is a block diagram of certain non-limiting components of the disclosed electronic identification, location tracking, communication and notification system that are generally involved in the registration of a beacon location;

FIG. 17 is a block diagram of certain non-limiting components of the disclosed electronic identification, location tracking, communication and notification system and also illustrating the steps/communications generally involved in the determination of a customer's presence at a location in a first non-limiting embodiment;

FIG. 18 is a block diagram of certain non-limiting components of the disclosed electronic identification, location tracking, communication and notification system and also illustrating the steps/communications generally involved in the determination of a customer's presence at a location in a second non-limiting embodiment;

FIG. 19 is a block diagram and process flow for the notification rules engine of the disclosed electronic identification, location tracking, communication and notification system;

FIG. 20 is a block diagram of certain non-limiting components of the disclosed electronic identification, location tracking, communication and notification system and also illustrating the steps/communications generally involved in the determination and delivery of notifications;

FIG. 21 is a block diagram of certain non-limiting components of the disclosed electronic identification, location tracking, communication and notification system and also illustrating the steps/communications generally involved in the determination and delivery of notifications in an alternative embodiment;

FIG. 22 is a block diagram of certain non-limiting components of the disclosed electronic identification, location tracking, communication and notification system and also illustrating the steps/communications generally involved in the presence determination at a location rules engine;

FIG. 23 is a block diagram of certain non-limiting components of the disclosed electronic identification, location tracking, communication and notification system and also illustrating the steps/communications generally involved in the ordering of goods and/or services from the App;

FIG. 24 is a block diagram of certain non-limiting components of the disclosed electronic identification, location tracking, communication and notification system and also illustrating the steps/communications generally involved in the delivery of goods and/or services to the customer's current location; and FIG. 25 is a block diagram of certain non-limiting components of the disclosed electronic identification, location tracking, communication and notification system and also illustrating the steps/communications generally involved for a customer to opt-out of rating/monitoring by a facility, company and/or business.

DETAILED DESCRIPTION

Figure 13:
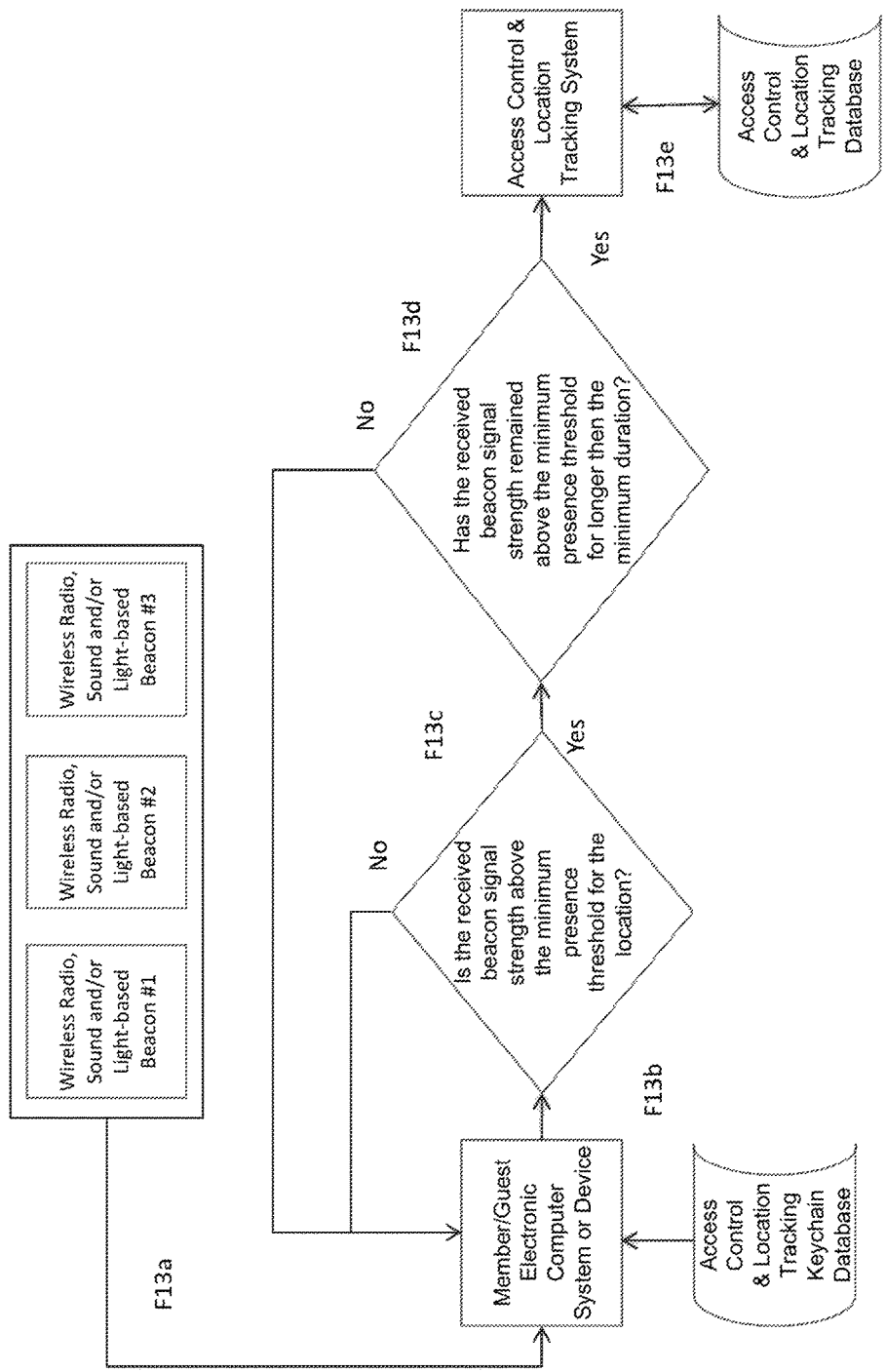
FIG. 13 is a block diagram of certain non-limiting components for determining presence at a specific location and also illustrating the steps/communications generally involved in selecting the appropriate digital key for the specific location.

FIG. 1 shows one method for allowing a member to register their computer system or electronic device with the disclosed access control & location tracking system. This initial registration process preferably allows a member to electronically receive digital/electronic access keys as well as grant a guest access to a controlled access location, and subsequently track the guest's location within that area.

At step F1a, a member registers their electronic computer system or electronic device with the disclosed access control & location tracking system. This enables the member to use their computer system or electronic device to access restricted locations and provide their guests with temporary access to controlled access areas. It also allows the member to use their electronic device to track their guest's location within the controlled access area, and confirm their guest's arrival and departure at a given permitted location. Registration can be accomplished in a number of non-limiting ways. As one non-limiting example, the system administrator can register the members directly through the programmed software using a form and then have the members credentials sent to the member via SMS, MMS, Email, Voice, Mail or other delivery methods. Alternatively, the member can download the software application (app) to their electronic device, register through a form on the app and then the system administrator can approve or deny the registration request. Once the software app is installed on the electronic device and registration is accepted by the system administrator the members digital/electronic keys can be downloaded by the member to the electronic device and stored in their electronic keychain database on their electronic device. The application/database storing the digital/electronic keys then transmits the key to the Access Control & Location Tracking System via any of the wireless radio, light or sound based technologies (wifi, Bluetooth, lifi, rfid, etc.)

At step F1b, the access control & location tracking system is programmed to record permissions afforded to and requested by members and retains and electronically stores those permissions in the Access Control and Tracking Location database. The system utilizes this database's record of members, guests, access rights, locations, and permissions to determine and then grant the level of access to a member, a guest requested by a member, and to provide the real time tracking and confirmation of member and guest movements.

At step F1c, the access control system administrator oversees the access control & location tracking system. Through the system, the administrator can track all member and guest movements, rights, and access. This allows the administrator to employ the necessary level of security or emergency response to protect the safety of members and guests, should a member or guest go beyond the scope of their access. The administrator is notified of the device registration request and can grant or revoke permission to use the registered device. Though not limiting, in the preferred embodiment, the system can be programmed such that the administrator receives device registration requests from a member. The system can also be programmed such that guest registration requests go directly to the member they are requesting access from (though the system can also be programmed to permit the administrator to override, approve and/or cancel decisions made by the member concerning the guest's request).

At step F1d, the access control & location tracking system electronically sends the member's electronic computer system or electronic device the digital access key assigned to them. It also provides the member's electronic computer system or electronic device with real time information on their guest's or other associated/authorized member's whereabouts. This allows the member to confirm that the guest reached their destination.

At step F1e, the digital access key is stored in the electronic keychain database on the member's electronic computer system/device. A similar keychain database on a guest's electronic device is created to store any digital access key(s) granted to a guest through the system.

FIG. 2 illustrates how a member provides a guest access to the controlled access location. The member electronically sends the guest a digital electronic key, which provides the guest with access to a controlled access area limited by the parameters set by the member.

At step F2a, a member electronically sends a request to the access control computer system that a digital key be generated and electronically sent to a guest. The member enters any limitations to be placed on the guest's access to the controlled area in the request. An administrator can also be permitted to enter additional access restrictions for the guest. In one non-limiting embodiment, the system can be programmed to provide a form containing a series of checkboxes for each location controlled by the system that the member can select from. A date and time module can also be provided for allowing the member to indicate the starting date and time and ending date and time for the guest's digital key. Further detail on the permissions and limitations a member can place on a key for a guest is discussed in connection with FIG. 7.

At step F2b, the access control and location computer system records the member's request and automatically enters it into the access control database. This information is electronically stored and later used by the Access Control & Location Tracking system when the guest receives their access key and enters the secured access location.

At step F2c, the access control and location computer system can directly send the guest an electronic key to their smartphone or other electronic device via electronic communication methods including but not limited to direct data connection, SMS, Email, MMS and voice. A confirmation electronic message can be sent to the member to inform them that their guest's key was approved and sent to the guest. Alternatively, the system can be programmed that the guest key is first sent to the member, and the member forwards it to the guest. The key is imported to a software application, which is stored locally on the guest's device. This application acts as an electronic keychain of access keys. In one non-limiting embodiment, the digital key can be an electronic file, which is preferably encrypted. The key can be auto-imported where it is sent to person's electronic device through an app directly that is downloaded on the electronic device or manually added if the key is sent through SMS or email. For the manual method, the guest can click on the file and than have an app import the key to the local device database. Once the guest receives the key, the guest has all access rights, which have been granted to them by a member, as seen/discussed in step F2a and FIG. 7. The guest can have a key provided by multiple members within the same Access Control & Location Tracking System location or keys for multiple locations (with separate instances of the Access Control & Location Tracking System). As a non-limiting example, if the guest is a service provider (i.e. plumber, electrician, personal trainer, delivery person, etc.) the guest may need to have keys from multiple members at any given time. Also in some instances a person can be a member at one location and a guest at other locations and may have member key(s) and guest(s) keys on his or her electronic keychain database stored on his or her electronic device.

At step F2d, the electronic key is electronically stored in the access control & location tracking keychain database on the guest's device.

FIG. 3 illustrates how the system grants or denies access to a member or guest based on the electronic key on their device.

At step F3a, the member or guest attempting to enter a controlled access location will have an electronic key on their device, such as the electronic key the guest receives from the steps described in FIG. 2. Through a wireless radio, sound and/or light enabled application, their device will retrieve all electronic keys stored in the device's keychain database and transmit them to any wireless radio, sound and/or light-based beacons in an immediate proximity to the controlled access area entrance. FIG. 9 shows one non-limiting embodiment where the electronic device can be configured for its owner to manually select the digital key to transmit (i.e. virtual clicker), while FIG. 10 shows another non-limiting embodiment where the electronic device can be configured to auto-sense that it is at a beacon and then have the user manually select the digital key to transmit to the beacon and FIG. 11 shows a further non-limiting embodiment where the electronic device can be configured to automatically sense that it is at a beacon and then automatically send the digital key(s) to the beacon. The member or guest can also choose which specific key to transmit if so configured and desired. The key can be manually chosen via a user interface provided by the software installed on the member's or guest's electronic device or it can also just send all keys available on the users keychain to the system and it will continue to check each key on the keychain to see if one grants them access for the location, date and time. The system can be programmed such that access denial is only given after all available keys are checked. Preferably, the built in capabilities of conventional smartphones/electronic devices can be used, as they currently come with Wifi, Bluetooth and sometimes NFC radios or InfraRed sensors, and some also have ultrasonic capable microphones or lifi built in. If not provided, these technologies can be provided or later acquired by the electronic device. The Access Control and Location Tracking system, through instructions provided by the programmed software, accesses the radios and other communication hardware available on the electronic device and uses them as needed.

At step F3b, the member or guest's device will communicate through wireless radio, sound and/or light-based beacons with the access control and location tracking system. The system will then recognize that a device with the application is in proximity to a controlled access area and retrieve the key(s) stored on said device. As mentioned above, the software can be configured to automatically send the keys or the member/guest can choose which key to send. When the software on the member/guest's electronic device is in range of a beacon, it can receive a signal triggering it to send the keys in its keychain database to the access control & location tracking database.

At step F3c, the access control & location tracking system automatically searches though the access control & location tracking database for permissions granted to the member or guest from the provided key. The member or guest will be permitted to enter areas based on these permissions.

At step F3d, when a member or guest wishes to enter into a controlled access area, the system will determine whether the member or guest has a valid key allowing entry. If a valid key is presented, access is granted and an electronic signal is sent to open the access barrier such as a Gate, Door, Elevator or other Entryway. Additionally, notification is electronically sent to Security Staff through a computer screen or other electronic device. The access control & location tracking database is updated with details pertaining to the access event such as the key code, date, time and location.

At step F3e, if a valid key is not presented, then access will be denied and notification is sent to Security Staff through a computer screen or other electronic device. The access control & location tracking database is updated with details pertaining to attempted access event including the key code, date, time and location. Optionally, the Access Control and Location Tracking system can be programmed that where a guest or member attempts to enter an area where they are not approved (i.e. when access denied by the system), all of some of the access permissions that they have been granted are suspended or terminated, to permit the administrator or other proper personnel (i.e. security) to investigate the denial (i.e. determine whether it was an accident or that the member/guest has bad motives). The results of the investigation can determine whether the previous permissions are granted again or unsuspended by the system.

FIG. 4 demonstrates how the system determines whether a member or guest is in an authorized or unauthorized location on a continuous basis.

At step F4a, physical wireless radio, sound and/or light-based beacons are placed throughout a controlled access area. These are arranged so that when a member or guest with a wireless radio, sound and/or light enabled device and the permissions application running enters the area, they are preferably constantly within range of a beacon. The member or guests access key can be automatically electronically retrieved from the keychain database stored in their electronic device and transmitted by the wireless radio, sound and/or light-based beacons to the access control & location tracking system preferably in continuous intervals.

At step F4b, the access control & location tracking system receives the access key(s) and compares the key(s) to the access control & location tracking database to determine the permissions afforded to each specific key that is received.

At step F4c, if the member or guest is in an authorized location based on the permissions retrieved in F4b, then the system will update the database to reflect the current location of the member or guest.

At step F4d. If the member or guest is in an unauthorized location, then the system administrator and/or security staff is notified. In the case of a guest, the member who granted the guest access can be notified as well that the guest has gone beyond the parameters of their authorization. The alert is generated by the access control & location tracking system and can be sent through computer, voice, email, IM, SMS, MMS, pager or other communication method. The access control & location tracking database can also be updated with the member or guest's current location. Additionally, the termination or suspension of all or some of the guest/member's access permissions as described above can also be performed by the Access Control & Location Tracking system.

FIG. 5 demonstrates how the system determines whether a member or guest has arrived at their authorized location after being granted access into the controlled access area as described in FIG. 3.

At step F5a, physical wireless radio, sound and/or light-based beacons are placed throughout a controlled access area to determine specific locations within the access area. These are arranged so that when a member or guest with a wireless radio, sound and/or light enabled device and the permissions application running enters the area, they are preferably constantly within range of a beacon. The member or guests access key can be automatically electronically retrieved from the keychain database stored in their electronic device and transmitted by the wireless radio, sound and/or light-based beacons to the access control & location tracking system preferably in continuous intervals.

At step F5b, the access control & location tracking system receives the access key(s) as well as location of the device based on which wireless radio, sound and/or light-based beacons received the key and compares the key(s)/location to the access control & location tracking database.

At step F5c, if the access control & location tracking system determines that the location of the member or guest is at the final authorized location based on the permissions retrieved in F5b, then the system will update the database.

At step F5d, if the access control & location tracking system determines that the location of the member or guest is not at the final authorized location within the time allotted based on the permissions retrieved in F5b, then the system administrator and/or security staff is notified. In the case of a guest, the member who granted the guest access can be notified as well that the guest has not arrived at their authorized location within the time period allotted. The alert is generated by the access control & location tracking system and can be sent through computer, voice, email, IM, SMS, MMS, pager or other communication method. The access control & location tracking database is also updated with the member or guest's current location.

FIG. 6 demonstrates how the system provides navigational assistance to members and/or guests after being granted access into the controlled access area as described in FIG. 3.

At step F6a, physical wireless radio, sound and/or light-based beacons are placed throughout a controlled access area to determine specific locations within the access area. These are arranged so that when a member or guest with a wireless radio, sound and/or light enabled device and the permissions application running enters the area, they are preferably constantly within range of a beacon. The member or guests access key can be automatically electronically retrieved from the keychain database stored in their electronic device and then transmitted by the wireless radio, sound and/or light-based beacons to the access control & location tracking system in preferably continuous intervals.

At step F6b, the access control & location tracking system receives the access key(s) as well as location of the device based on which wireless radio, sound and/or light-based beacons received the key and compares the key(s)/location to the access control & location tracking database.

At step F6c, if the access control & location tracking system determines that the location of the member or guest is at the final authorized location based on the permissions retrieved in F6b, then the system will update the database.

At step F6d, if the access control & location tracking system determines that the location of the member or guest is not at the final authorized location based on the permissions retrieved in F5b, then it updates the access control & location tracking database with the member or guests current location. The system then calculates the possible routes to the final authorized location from the current location of the member or guest. The route information is electronically sent to the member or guests device through computer, voice, email, IM, SMS, MMS, pager or other communication method. Visual interpretation and presentation of the route may also be provided, such as, but not limited to through the electronic device's screen or display. Additionally, the termination or suspension of all or some of the guest/member's access permissions as described above can also be performed by the Access Control & Location Tracking system where the guest/member does not reach a specific location in the allotted or predetermined amount of time.

FIG. 7 demonstrates how a member or system administrator can create a new digital key and assign the specific permissions and notifications for the new digital key. This process can also be utilized to edit permissions and notifications for existing keys.

At step F7a, the "Create New Key" function is selected within the access control & location tracking system by a user with key creation privileges such as a system administrator or member. Preferably, the system administrator or member will have previously signed on or logged in to the system so that their key creation privileges are recognized by the system. Guests are preferably not allowed to create new keys, though such is not considered limiting, and the system can be programmed where a guest could create a key or transfer his or her key to another keychain in certain or limited situations (i.e. husband to wife or vice versa, etc.).

At step F7b, the access control & location tracking system electronically queries the system database to determine existing key recipients as well as available locations, access points, and the rule set assigned to the system administrator or member creating the new key. The user can only create new keys that they themselves have been granted permissions for. As a non-limiting example, if a given user is not allowed access to a specific location, said user would not be able to create a key granting access to that specific location. The screens and options available for creating a key in F7c through F7l are customized based on the granted permissions for the user creating the key. Therefore, another user who has more permissions than the user presented with the options in F7c through F7l could be presented with additional options and screens not shown in F7c through F7l. Similarly, another user who has less permissions may be presented with less than all of the options and screens shown in F7c through F7l. Additionally, the system can be programmed such that the options specified in F7c through F7l work in conjunction with each other, so for example, if a single date is specified along with a specific time span, the key can only be valid for that time span on the specified date.

At step F7c, the user enters or selects the recipient's name and contact information from the list of available recipients retrieved in F7b. The specific data elements entered will depend on the electronic method desired to send the digital key to the recipient. For example, if email delivery is selected, then a name and email address is required for the recipient but if an SMS or voice call is selected, a name and phone number for the recipient is required.

At step F7d, the user selects the type of key recipient for this new key. Keys can be created for Members, Guests, Administrators and/or Public Service personnel such as Police, Fire, Utility and Government Agency workers, though such is not considered limiting, and other types of individuals based on status, employment, etc. can also be digital key recipients.

At step F7e, the user specifies the number of times this digital key can be used. Keys can be created for one-time use only, for a specific number of times or for an unlimited number of times.

At step F7f, the user specifies the permissible access dates for the digital key. Keys can be created for a single time span, multiple time spans, or without a time restriction.

At step F7g, the user specifies the permissible access times of day/night for the digital key. Keys can be created for a single time span, multiple time spans, or without a time restriction.

At step F7h, the user specifies the permissible access locations and entry points for the digital key. Keys can be created for a single location/entry point, multiple locations/entry points, or all locations and entry points.

At step F7i, next the user can select if notifications are to be sent related to the usage of this digital key. This function would typically apply to keys generated for guests or public service personnel. If the user does not wish to configure any notifications related to the use of this key, the data and entries for the specific digital key created are saved in the electronic database and steps F7j through F7m are skipped. If they user wishes to create notifications related to the use of this key, then the user can preferably proceed to F7j.

At step F7j, the user selects the type(s) of notifications to be sent. As non-limiting examples, notifications can be sent based on the usage of the key to gain entry to a restricted location, upon arrival at a permitted location, when the key recipient does not arrive at a specific location or if the key recipient has navigated off course from the point of entry to the final authorized location.

At step F7k, the user selects the method(s) of notifications to be sent. Notifications can be sent via SMS/MMS, Email, Voice, or on-screen at the access control & location tracking system or directly through the access control & location tracking system software on the administrator or member's electronic computer system/device.

At step F7l, the user selects or enters the notification recipient(s). Notification recipient(s) can be selected from a list of existing administrators and members or entered with the recipient(s) name and contact information. For example, if an email notification is selected, then a name and email address is preferably provided for the recipient but if an SMS or voice call is selected, a name and phone number for the recipient is preferably provided.

At step F7m, the digital key with all permission and notification settings is electronically saved in the system database.

At step F7n, the access control & location tracking system electronically delivers the newly created (or modified) key to the recipient according to the contact information obtained in F7c.

FIG. 8 demonstrates how a member, guest, system administrator or public service personnel can receive digital keys from multiple access control & location tracking systems and store those keys in an electronic keychain database on their electronic computer system or device. The multiple systems can be associated with multiple locations. In one non-limiting example, one location can be residential community 1, the next location condo building 2, the next location a commercial office building. In some instances, the beacons can be used in multiple systems (i.e. lobby of a commercial office building where multiple systems are installed in the building for different companies that have office space in the building, etc.)

At step F8a, one or more access control & location tracking systems generates digital key(s) for a member, guest, administrator or public service personnel as described above. The digital keys are electronically sent to a computer system or device belonging to the member, guest, administrator or public service personnel.

At step F8b, the digital keys sent to the member/guest's electronic computer system or device are electronically stored in the keychain database also stored on the device.

The system can operate similar for members as it does for guests, with the exception that a member can be permitted to create and provide electronic guest keys to others, granting no more than the member's own level of privileges and/or access. Guest can preferably only use the electronic key provided by a member or another authorized user of the system, but preferably cannot create electronic guest keys for other guests or permit another electronic device to use the electronic guest key they were provided with (i.e. cannot forward the electronic guest key to another guest). However, the system can also be programmed to permit a guest to transfer their electronic guest key to another authorized guest already listed in the system (i.e. husband to wife or vice versa, parent to child, etc.), such as where only one guest key is created.

FIG. 9 illustrates how a member or guest would manually choose a key from their device's keychain database to transmit to an access control & location tracking system.

At step F9a, the member or guest attempting to enter a controlled access location will have an electronic key(s) on their device, such as the electronic key(s) the guest receives from the steps described in FIG. 2. The electronic key(s) will be stored in the keychain database on the member's/guest's electronic device. The member or guest opens the Access Control & Location Tracking system application on their electronic device and selects the option to manually transmit a key. The application on the device queries the keychain database on said device to determine which keys are stored and available for transmission.

At step F9b, if no access key has been selected for transmission, the application on the member or guest's electronic device will continue to wait for authorization to transmit a selected key.

At step F9c, if the member or guest selects a key and authorizes its transmission, the device will retrieve the selected electronic keys stored in the device's keychain database and transmit it to any wireless radio, sound and/or light-based beacons in an immediate proximity to the controlled access area entrance. Preferably, the built in capabilities of conventional smartphones/electronic devices can be used, as they currently come with Wifi, Bluetooth and sometimes NFC radios or InfraRed sensors, and some also have ultrasonic capable microphones or lifi built in. If not provided, these technologies can be provided to, downloaded or later acquired by the electronic device. The Access Control and Location Tracking system, through instructions provided by the programmed software, accesses the radios and other communication hardware available on the electronic device and uses them as needed. The software can use any communication hardware (i.e. WiFi radios, Bluetooth radios, NFC radios, LiFi, IR, etc.) that is installed on the electronic device and can use the various hardware as needed to perform the functions of the software.

At step F9d, the member or guest's transmitted key is received through wireless radio, sound and/or light-based beacons and sent to the access control and location tracking system.

At step F9e, the access control & location tracking system automatically searches though the access control & location tracking database for permissions granted to the member or guest from the provided key. The member or guest will be permitted to enter areas based on these permissions.

At step F9f, if a valid key is presented, an electronic notification can be sent back to the member or guest's electronic device through the wireless radio, sound and/or light-based beacon indicating the key was validated and used.

At step F9g, the application on the member or guest's electronic device updates the access control & location tracking keychain database indicating the usage of the key.

At step F9h, if a valid key is not presented, an electronic notification can be sent back to the member or guests' electronic device through the wireless radio, sound and/or light-based beacon indicating the key was not validated and asking the member or guest to select a new key to transmit.

At step F9i, the application on the member or guests' electronic device queries the access control & location tracking system keychain database for any other available keys and the process begins again at F9(b). If no other keys are available, the member or guest can then take steps to request a key as described in FIG. 1 or 12.

FIG. 10 illustrates how a member or guest would manually choose a key from their device's keychain database to transmit to an access control & location tracking system after prompting by a wireless radio, sound and/or light-based beacon.

At step F10a, wireless radio, sound and/or light-based beacon(s) transmit a signal that is received by the member or guest's electronic device. The application installed and running on the member or guests' electronic device will receive the signal from the beacon(s) and prompt, preferably automatically, the member or guest that they are in the proximity of the beacon(s) and to select a key for transmission to the beacon(s).

At step F10b, the member or guest attempting to enter a controlled access location will have an electronic key(s) on their device, such as the electronic key(s) the guest receives from the steps described in FIG. 2. The electronic key(s) will be stored in the keychain database on the device. The member or guest opens the Access Control & Location Tracking system application on their electronic device and selects the option to manually transmit a key. The application on the device queries the keychain database on the device to determine which keys are stored and available for transmission.

At step F10c, if no access key has been selected for transmission, the application on the member or guest's electronic device will continue to wait for authorization to transmit a selected key.

At step F10d, if the member or guest selects a key and authorizes its transmission, the device will retrieve the selected electronic keys stored in the device's keychain database and transmit it to any wireless radio, sound and/or light-based beacons in an immediate proximity to the controlled access area entrance. Preferably, the built-in capabilities of conventional smartphones/electronic devices can be used, as they currently come with Wifi, Bluetooth and sometimes NFC radios or InfraRed sensors, and some also have ultrasonic capable microphones or lifi built in. If not provided, these technologies can be provided or later acquired by the electronic device. The Access Control and Location Tracking system, through instructions provided by the programmed software that can be similar to those instructions referenced for FIG. 9, accesses the radios and other communication hardware available on the electronic device and uses them as needed. The software can use any communication hardware (i.e. WiFi radios, Bluetooth radios, NFC radios, LiFi, IR, etc.) that is installed on the electronic device and can use the various hardware as needed to perform the functions of the software.

At step F10e, the member or guest's transmitted key is received through wireless radio, sound and/or light-based beacons and sent to the access control and location tracking system.

At step F10f, the access control & location tracking system automatically searches though the access control & location tracking database for permissions granted to the member or guest from the provided key. The member or guest will be permitted to enter areas based on these permissions.

At step F10g, if a valid key is presented, an electronic notification can be sent back to the member or guest's electronic device through the wireless radio, sound and/or light-based beacon indicating the key was validated and used.

At step F10h, the application on the member or guest's electronic device updates the access control & location tracking keychain database indicating the usage of the key.

At step F10i, if a valid key is not presented, an electronic notification can be sent back to the member or guests' electronic device through the wireless radio, sound and/or light-based beacon indicating the key was not validated and asking the member or guest to select a new key.

At step F10j, the application on the member or guests' electronic device queries the access control & location tracking system keychain database for any other available keys as in F10(b) and the process repeats from that point. If no other keys are available, the member or guest can then take steps to request a key as described in FIG. 1 or 12.

FIG. 11 illustrates how a key from a member or guests' electronic device keychain database is automatically transmitted to an access control & location tracking system after prompting by a wireless radio, sound and/or light-based beacon.

At step F11a, wireless radio, sound and/or light-based beacon(s) transmit a signal that is received by the member or guests electronic device. The application installed and running on the member or guests' electronic device will receive the signal from the beacon(s) and begin to search for a key to transmit. Each beacon in the system can send out a signal that the application on the electronic device can read. That signal can contain information such as, but not limited to, the name of the beacon, the organization it belongs to and location of the beacon. This same location information can be stored in the keys that are generated.

At step F11b, the member or guest attempting to enter a controlled access location will have an electronic key(s) on their device, such as the electronic key(s) the guest receives from the steps described in FIG. 2. The electronic key(s) will be stored in the keychain database on the device. The member or guest opens or has running, the Access Control & Location Tracking system application on their electronic device and said application is or has previously been configured to automatically transmit a key(s). The application on the device queries the keychain database on said device to determine which keys are stored and available for transmission.

At step F11c, if no access key exists in the database for this location, the member or guest is notified through the access control & location tracking application installed and running on their electronic device. The member or guest can then take steps to request a key as described in FIG. 1 or 12.

At step F11d, if the access control & location tracking system application on the member or guests' electronic device locates a key for the location, it will retrieve the selected electronic key stored in the device's keychain database and transmit it to any wireless radio, sound and/or light-based beacons in an immediate proximity to the controlled access area entrance. In one embodiment for locating the key, the software can compare the location and other information it received from the beacon to search the keychain database. Preferably, the built in capabilities of conventional smartphones/electronic devices can be used, as they currently come with Wifi, Bluetooth and sometimes NFC radios or InfraRed sensors, and some also have ultrasonic capable microphones or lifi built in. If not provided, these technologies can be provided or later acquired by the electronic device. The Access Control and Location Tracking system, through instructions provided by the programmed software that can be similar to the those instructions referenced for FIG. 9, accesses the radios and other communication hardware available on the electronic device and uses them as needed. The software can use any communication hardware (i.e. WiFi radios, Bluetooth radios, NFC radios, LiFi, IR, etc.) that is installed on the electronic device and can use the various hardware as needed to perform the functions of the software.

At step F11e, the member or guest's transmitted key is received through wireless radio, sound and/or light-based beacons and sent to the access control and location tracking system.

At step F11f, the access control & location tracking system automatically searches though the access control & location tracking database for permissions granted to the member or guest from the provided key. The member or guest will be permitted to enter areas based on these permissions.

At step F11g, if a valid key is presented, an electronic notification can be sent back to the member or guest's electronic device through the wireless radio, sound and/or light-based beacon indicating the key was validated and used.

At step F11h, the application on the member or guest's electronic device updates the access control & location tracking keychain database indicating the usage of the key.

At step F11i, if a valid key is not presented, an electronic notification can be sent back to the member or guests' electronic device through the wireless radio, sound and/or light-based beacon indicating the key was not validated and prompting the access control & location tracking system application to select a new key to transmit.

At step F11j, the application on the member or guests' electronic device queries the access control & location tracking system keychain database for any other available keys as in F11(b) and the process repeats from that point.

FIG. 12 shows one method for allowing a guest to request a key from a member.

At step F12a, a guest opens the access control & location tracking system application on their electronic device. Preferably the software app is previously downloaded electronic device and can be used at various different locations where the system is installed. Furthermore, if the person has used the app in the past for access, the app will already be on their electronic device for subsequent uses whether at the previous location or other locations where the system is installed. Through the application, the guest selects or enters the member information for which the guest would like to request a key from. The guest then selects a button to request a key and a key request is transmitted to the access control & location tracking system through any available form of electronic communication and data transfer including but not limited to through a wireless radio, sound or light enabled beacon, wired or wireless internet connection, voice call, SMS, Email or MMS. Furthermore, other non-limiting examples of ways a guest can request a key from a member include, but are not limited to, through a member name directory similar to a call box a community allows a person to scroll through the names of the residents and a method to contact them. The members' address, phone numbers, email addresses and other information does not need to be shown to the guests in order for the guests to use the system to facilitate communication. The system can also be configured so that the directory can be turned off if desired, or the directed limited to those who are at the same location as the guest. Also, the software can be provided with an address book functionality to store member and guests names for future use, which can be useful for a member who needs to frequently issues keys to the same person or a guest who frequently requests access from specific people.

At step F12b, the access control and location computer system records the guest's request and automatically enters it into the access control & location tracking system database. The Access Control & Location Tracking system also retrieves the member's information so that it may forward the request to the member's electronic device.

At step F12c, the Access Control & Location Tracking system transmits the guest key request to the member's electronic device through any available form of electronic communication and data transfer including but not limited to through a wireless radio, sound or light enabled beacon, wired or wireless internet connection, voice call, SMS, Email or MMS.

At step F12d, a member receives the guest key request and proceeds to enter any limitations to be placed on guest's access to the controlled area in the request. An administrator can also be permitted to enter additional access restrictions for the guest. In one non-limiting embodiment, the system can be programmed to provide a form containing a series of checkboxes for each location controlled by the system that the member can select from. A date and time module can also be provided for allowing the member to indicate the starting date and time and ending date and time for the guest's digital key. Further detail on the permissions and limitations a member can place on a key for a guest is discussed in FIG. 7.

At step F12e, the member transmits the newly created guest key from their electronic device to the Access Control & Location Tracking system through any available form of electronic communication and data transfer including but not limited to through a wireless radio, sound or light enabled beacon, wired or wireless internet connection, voice call, SMS, Email or MMS.

At step F12f, the Access Control & Location Tracking system receives the guest key and stores it in the Access Control & Location Tracking System Database.

At step F12g, the access control and location computer system can directly send the guest an electronic key to their smartphone or other electronic device via electronic communication methods including but not limited to direct data connection, SMS, Email, MMS and voice. A confirmation electronic message can be sent to the member to inform them that their guest's key was approved and sent to the guest. Alternatively, the system can be programmed that the guest key is first sent to the member, and the member forwards it to the guest. The key is imported to a software application, which can be the same software application referenced in Step 12(a), which is stored locally on the guest's device. This application acts as an electronic keychain of access keys. Once the guest receives the key, the guest has all access rights, which have been granted to them by a member, as seen in F2a, F12d and FIG. 7. The guest can have a key provided by multiple members within the same Access Control & Location Tracking System location or keys for multiple locations (with separate instances of the Access Control & Location Tracking System). As a non-limiting example, if the guest is a service provider (i.e. plumber, electrician, personal trainer, delivery person, etc.) the guest may need to have keys from multiple members at any given time. Also in some instances a person can be a member at one location and a guest at other locations and may have member key(s) and guest(s) keys on his or her electronic keychain database stored on his or her electronic device.

At step F12h, the electronic key is electronically stored in the access control & location tracking keychain database on the guest's device.

FIG. 13 demonstrates how the system determines presence at a location to determine the proper digital key to utilize at a specific location and time.

At step F13a, physical wireless radio, sound and/or light-based beacons are placed throughout a controlled access area to determine specific locations within the access area. These are arranged so that when a member or guest with a wireless radio, sound and/or light enabled device and the permissions application running on their device enters the area, they are preferably constantly within range of a beacon.

At step F13b, the member or guests wireless radio, sound and/or light enabled device queries the keychain database stored in their electronic device to determine what location the device is currently located at. This query is done based on the identification information received by the device from the beacon. Preferably, the beacon, at a minimum, transmits a unique identifier to the device. This allows for the beacon's specific location to be determined or known by the device such that the device determines the proper digital key to retrieve from the keychain database for the specific location. Preferably, the device will also learn or determine what the power and duration configuration settings are for the specific location from the signal transmitted by the beacon for the location and/or from information stored in the keychain database associated with the specific location.

At step F13c, the member or guests wireless radio, sound and/or light enabled device determines what the signal strength is from the received signal transmitted by the wireless radio, sound and/or light-based beacon(s). If the received signal strength, which can be measured in Decibels, Signal Strength Percentage or other non-limiting value, is not above the minimum specified or preprogrammed/preconfigured threshold for a given location as determined in F13b, the member or guests wireless radio, sound and/or light enabled device will continue to scan for signals or transmissions from the wireless radio, sound and/or light-based beacon(s) and will make similar signal strength determinations for subsequent signals/transmissions it receives. If the received signal strength is above the minimum threshold for a given location, the system continues to the next step.

At step F13d, the member or guests wireless radio, sound and/or light enabled device begins a timer to determine the length of time that a wireless radio, sound and/or light-based beacon's signal is received above the minimum signal strength threshold. If the received signal strength falls below the minimum threshold before the minimum duration has elapsed, the member or guests wireless radio, sound and/or light enabled device will continue to scan for signals or transmissions from the wireless radio, sound and/or light-based beacon(s) and will make similar signal strength and/or duration determinations for subsequent signals/transmissions it receives. If the received signal strength remains above the minimum threshold as determined in F13b, for longer than the minimum duration then the member or guests wireless radio, sound and/or light enabled device will transmit the key retrieved n F13b to the access control & location tracking system.

At step F13e, the access control & location tracking system will update the access control & location tracking database regarding valid and/or invalid signal determinations from steps 13c and/or 13d. It can then grant or deny access based upon the configured permissions for the particular member or guest.

Figure 14:
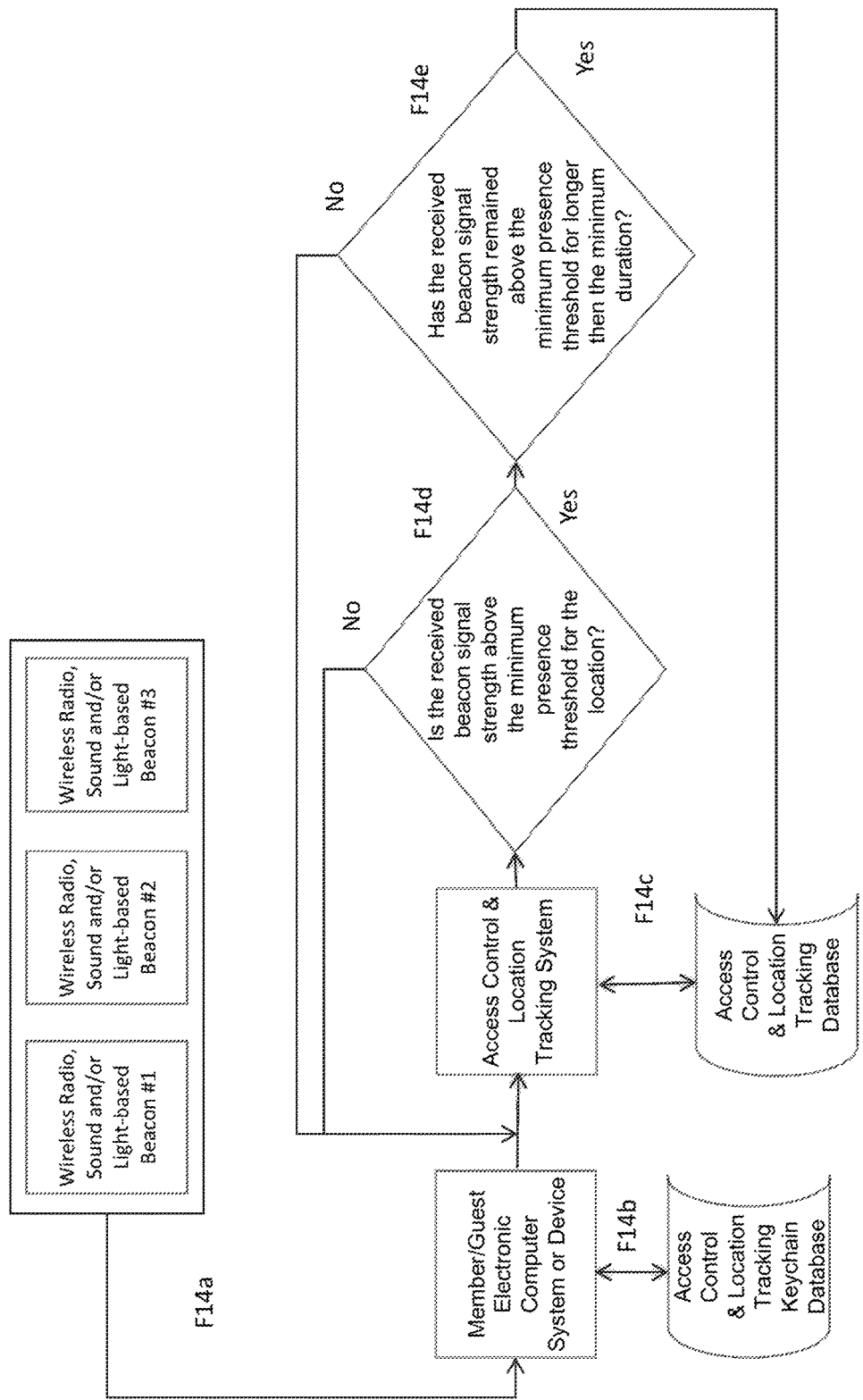
FIG. 14 is a block diagram of certain non-limiting components for determining presence at a specific location and also illustrating another embodiment of the steps/communications generally involved in selecting the appropriate digital key for the specific location.

FIG. 14 demonstrates another method for how the system determines presence at a location to determine the proper digital key to utilize at a specific location and time.

At step F14a, physical wireless radio, sound and/or light-based beacons are placed throughout a controlled access area to determine specific locations within the access area. These are arranged so that when a member or guest with a wireless radio, sound and/or light enabled device and the permissions application running on their device enters the area, they are preferably constantly within range of a beacon.

At step F14b, the member or guests wireless radio, sound and/or light enabled device queries the keychain database stored in their electronic device to determine what location the device is currently located at. This query is done based on the identification information received by the device from the beacon. Preferably, the beacon, at a minimum, transmits a unique identifier to the device. This allows for the beacon's specific location to be determined or known by the device such that the device determines the proper digital key to retrieve from the keychain database for the specific location. Preferably, the device will also learn or determine date and time information.

At step F14c, the member or guests wireless radio, sound and/or light enabled device transmits its identification, location and what the signal strength is from the signal/transmission it received from the wireless radio, sound and/or light-based beacon(s) to the Access Control & Location Tracking System.

At step F14d, The Access Control & Location Tracking System determines what the power and duration configuration settings are for the specific location.

At step F14e, the Access Control & Location Tracking System compares the configured settings retrieved in F14d to the received signal strength being reported by the member or guests wireless radio, sound and/or light enabled device. If the received signal strength, which can be measured in Decibels, Signal Strength Percentage or other non-limiting value, is not above the minimum specified threshold for a given location as determined above, the Access Control & Location Tracking System will continue to scan for signals or transmissions from the member or guests wireless radio, sound and/or light enabled device and will make similar signal strength determinations for subsequent signals/transmissions it receives. If the received signal strength is above the minimum threshold for a given location, the system continues to the next step.

At step F14f, the Access Control & Location Tracking System begins a timer to determine the length of time that a member or guests wireless radio, sound and/or light enabled device is transmitting a received signal strength from the wireless radio, sound and/or light-based beacon(s) above the minimum signal strength threshold. If the received signal strength falls below the minimum threshold before the minimum duration has elapsed, the Access Control & Location Tracking System will continue to scan for signals or transmissions from the member or guests wireless radio, sound and/or light enabled device and will make similar signal strength and/or duration determinations for subsequent signals/transmissions it receives. If the received signal strength is above the minimum threshold for a given location, the system will request that the digital key be sent by the member or guests wireless radio, sound and/or light enabled device to the access control & location tracking system.

At F14g, the member or guests wireless radio, sound and/or light enabled device transmits the digital key to the Access Control & Location Tracking System. It can then grant or deny access based upon the configured permissions for the particular member or guest. The access control & location tracking database can also be updated by the access control & location tracking system regarding valid and/or invalid signal determinations made by the access control & location tracking system FIG. 15 shows one method for allowing a customer to register their computer system or electronic device with the electronic identification, location tracking, communication and notification system of a particular company or business. This initial process allows a customer to be electronically and automatically tracked within the company's location, receive rewards program credits, order services delivered to their location and communicate with company employees.

At step F15a, a customer downloads and installs the Electronic Identification, Location Tracking, Communication & Notification Application "App" from their computer or any app store or marketplace including, but not limited to, the Apple App Store, Windows Store and Google Play marketplace. The App is downloaded to and installed on the customer's electronic system or device.

At step F15b, when the App is first opened, it prompts the user to register their electronic computer system or device with the electronic identification, location tracking, communication and notification system. This enables the customer to use their computer system or device to be automatically tracked within the customer's facility, communicate with the company, and order food, beverage or other products/services. Where the customer is interested in ordering food, beverage and/or other products or services, a menu or listing of the food, beverage and other products/services offered at the location can be displayed on the customer's electronic system or device to inform the customer of what is available at the location. If the user opens the App and does not wish to register the device then the App can operate in a non-registered mode that limits the services available on the device.

At step F15c, if the customer chooses to register the device with the electronic identification, location tracking, communication and notification system, a form can appear on the screen of the customer's electronic device prompting the customer for information including but not limited to their name, birthday, mailing address, email address, phone number, picture and/or credit card or other payment information for paying for goods/services ordered through the system. The system and software can also be designed such that multiple electronic systems and devices are associated with one account so that the rewards given to each electronic system or device are accumulated within one account (i.e. smartphones of a husband and wife and their children associated with one account so that all points or rewards earned based on activities of the family are accumulated into one account) and/or that payment information for one registered device can be used to pay for goods/services ordered by other electronic devices associated with the account. The required fields can be selected by the company and can depend on the specific company and needs of that company. The customer electronically submits the form when completed.

At step F15d, if during submission by the customer, the App determines that not all required fields are filled out, it will cause the electronic device to prompt the customer for the missing information. The user can resubmit the form with the missing information provided. At step F15e, once all required fields are provided and the form is electronically submitted by the customer, the electronically data is sent to the electronic identification, location tracking, communication and notification system.

At step F15f, the electronic identification, location tracking, communication and notification system electronically stores the customers form submissions along with some identifying information for the customer's device such as, but not limited to, the device name, UUID, MAC address, IP Address, or other unique identifiers. At step F15g, an electronic notification can be sent to the system administrator(s) via email, sms, mms, voice, fax or other electronic method of the new customer registration.

At step F15h, the system administrator can access the electronic identification, location tracking, communication and notification system to view and edit the new customer's profile. The system administrator can assign the customer to any group or list available, create notification rules for the customer or add information about the customer in its profile. At step F15i, any edits, if any, to the customer's profile by the system administrator can be electronically stored in the electronic identification, location tracking, communication and notification database.

FIG. 16 illustrates how a location is registered with the electronic identification, location tracking, communication and notification system.

At step F16a, a system administrator configures a wireless radio, sound and/or light-based beacon with information including, but not limited to, its name, unique identifier (MAC Address, UUID or similar), group/organization, unique number within an organization, location, wireless networks, etc. At step F16b, the configured wireless radio, sound and/or light-based beacon is physically installed at the configured location and tested to ensure its operability.

At step F16c, a system administrator electronically accesses the electronic identification, location tracking, communication and notification system to enter in the installed wireless radio, sound and/or light-based beacon's configuration and location information. Additional configuration of the beacon can also be performed at this step, which can include, but is not limited to, configuring notification settings, signal types, signal strengths, and device presence durations.

At step F16d, the wireless radio, sound and/or light-based beacon's configuration and location information can be electronically stored in the electronic identification, location tracking, communication and notification database.

FIG. 17 illustrates a first non-limiting embodiment of how the system determines the location of customer based on their registered device.

At step F17a, the wireless radio, sound and/or light-based beacons installed at various locations are constantly and automatically broadcasting their information including, but not limited to, its name, unique identifier (MAC Address, UUID or similar), group/organization, unique number within an organization, location, wireless networks, etc. At step F17b, the customer's electronic system or device with the Electronic Identification, Location Tracking, Communication & Notification Application "App" downloaded and running receives the broadcasted information from the wireless radio, sound and/or light-based beacons and automatically electronically transmits the information received, along with additional information including, but not limited to, signal type and strength to the Electronic Identification, Location Tracking, Communication & Notification system. This process repeats at configurable intervals so that the App can be frequently transmitting beacon information to the Electronic Identification, Location Tracking, Communication & Notification System.

At step F17c, the Electronic Identification, Location Tracking, Communication & Notification System queries the Electronic Identification, Location Tracking, Communication & Notification Database to determine the settings configured in step F17c for each of the beacon's information sent by the App on the customer's device. At step F17d, the Electronic Identification, Location Tracking, Communication & Notification System electronically analyzes the data received from the App and compares it against the retrieved configuration settings (See FIG. 22) for each wireless radio, sound and/or light-based beacon location it received information from. If the customer's device is not considered present at a location based on the electronic analysis of the Electronic Identification, Location Tracking, Communication & Notification System, it will continue to check the next data set received from the App and repeat this step. As a non-limiting example, the signal strength, which in one non-limiting example can be measured and calculated on a scale of 0 to 100% was configured to a minimum threshold of 80% (See block F22c of FIG. 22). This means that unless the customer's device receives a signal from the wireless radio, sound and/or light-based beacons greater than the 80% strength threshold, the customer will not be considered present at the beacon location by the Electronic Identification, Location Tracking, Communication & Notification System. Additionally, a minimum signal strength duration value may be specified for a given location (See Block F22d). If so configured, once the App on a customer's electronic system or device reports a signal strength value above the minimum threshold, it must continue to report a signal strength value above that minimum threshold for the configured duration threshold in order for the customer to be considered present at that beacon location by the system. Continuing from the non-limiting example above, if this minimum duration threshold is set to 20 seconds, the App must continue to report a signal strength value from a beacon above the 80% value for a duration of 20 consecutive seconds in order to consider the customer's electronic system or device present at that beacon location by the system.

At step F17e, if the analysis performed in F17d indicates that the customer's device is present at a given location, the status of that customer's device is updated with the information for such location. At step F17f, the Electronic Identification, Location Tracking, Communication & Notification Database prompts the Electronic Identification, Location Tracking, Communication & Notification System of the location confirmation so that any notification rules specified for that location and/or customer can be executed.

FIG. 18 illustrates an alternative embodiment of how the system determines the location of customer based on their registered device.

At step F18a, the customer's electronic system or device with the Electronic Identification, Location Tracking, Communication & Notification Application "App" downloaded and running is constantly and automatically broadcasting it's information including, but not limited to, its name, unique identifier (MAC Address, UUID or similar), group/organization, unique number within an organization, location, wireless networks, etc.

At step F18b, the wireless radio, sound and/or light-based beacons installed at various locations receive the broadcasted information from the App on the customer's device and transmits the information received, along with additional information including but not limited to signal type and strength to the Electronic Identification, Location Tracking, Communication & Notification system. This process repeats at configurable intervals so that the beacons are frequently automatically electronically transmitting customer device information to the Electronic Identification, Location Tracking, Communication & Notification System.

At step F18c, the Electronic Identification, Location Tracking, Communication & Notification System electronically queries the Electronic Identification, Location Tracking, Communication & Notification Database to determine the settings configured in F16c for each of the beacons information sent by the App on the customer's device.

At step F18d, the Electronic Identification, Location Tracking, Communication & Notification System analyzes the data received from the App and compares it against the retrieved configuration settings (See FIG. 22) for each wireless radio, sound and/or light-based beacon location it received information from. If the customer's device is not considered present at a beacon location based on the analysis of the Electronic Identification, Location Tracking, Communication & Notification System, it will continue to check the next data set received from the App and repeat this step. As a non-limiting example, the signal strength, which in one instance can be measured and calculated on a scale of 0 to 100% was configured to a minimum threshold of 80% (Block F22c of FIG. 22). This means that unless the customer's device receives a signal from the wireless radio, sound and/or light-based beacons greater than the 80% strength threshold, they will not be considered present at a location by the Electronic Identification, Location Tracking, Communication & Notification System. Additionally, a minimum signal strength duration value may be specified for a given location (Block F22d). If so configured, once the App on a customer's electronic system or device reports a signal strength value above the minimum threshold, it must continue to report a signal strength value above that minimum threshold for the configured duration threshold in order to be considered present at that location by the system. Continuing from the non-limiting example above, if this minimum duration threshold is set to 20 seconds, the App must continue to report a signal strength value above the 80% value for a duration of 20 consecutive seconds in order to consider the customer's electronic system or device present at that location by the system.

At step F18e, if the analysis performed in F18d indicates that the customer's device is present at a given location, the status of that customer's device is automatically updated with that locations information. At step F18f, the Electronic Identification, Location Tracking, Communication & Notification Database prompts the Electronic Identification, Location Tracking, Communication & Notification System of the location confirmation so that any notification rules specified for that location and/or customer can be executed.

FIG. 19 demonstrates how the notifications are configured within the Electronic Identification, Location Tracking, Communication & Notification System. This process can also be utilized to edit profile information and notifications for existing customers.

At step F19a, the Electronic Identification, Location Tracking, Communication & Notification System electronically queries the Electronic Identification, Location Tracking, Communication & Notification Database for the desired customer's existing information. This function can be typically reserved for a system administrator. At step F19b, the Electronic Identification, Location Tracking, Communication & Notification System displays the retrieved customer's profile information and verifies the accuracy of the information. The system administrator may also enter new information in the customer's profile if so desired.

At step F19c, once the customer's profile information is verified and/or updated, the system administrator may add the customer to one or more groups or lists maintained within the system. The system may also allow for default groups/lists to be assigned to all customers of a facility. At step F19d, once the groups and/or lists are selected, the system administrator, through the system, has the option of sending electronic notifications upon confirmation of a customer's presence as described in FIGS. 17 and 18, at any location configured in the Electronic Identification, Location Tracking, Communication & Notification System. If no notifications are desired, the customer's profile information can be updated in the Electronic Identification, Location Tracking, Communication & Notification Database.

At step F19e, if the system administrator desired to configure electronic notifications for the customer, through the system, they configure the electronic notification recipient(s) and type of electronic notification (though not limiting and a visual or audio notification could also be given) to be sent upon confirmation of their presence as described in FIGS. 17 and 18, at any location configured in the Electronic Identification, Location Tracking, Communication & Notification System. More than one notification can be configured for a given customer. At step F19f, the customer's profile information can be updated in the Electronic Identification, Location Tracking, Communication & Notification Database along with the configured notification settings.

FIG. 20 demonstrates how the system determines if a notification is to be delivered, where the notification is to be delivered and how the notification is to be delivered.

At step F20a, the customer's electronic system or device with the Electronic Identification, Location Tracking, Communication & Notification Application "App" downloaded and running can be constantly and automatically broadcasting the customer's electronic device information including, but not limited to, its name, unique identifier (MAC Address, UUID or similar), group/organization, unique number within an organization, location, wireless networks, etc. At step F20b, the wireless radio, sound and/or light-based beacons installed at various locations electronically receive the broadcasted information from the App on the customer's device and automatically electronically transmit the information received, along with additional information including but not limited to signal type and strength to the Electronic Identification, Location Tracking, Communication & Notification system. This process repeats at configurable intervals so that the beacons are frequently and automatically electronically transmitting customer device information to the Electronic Identification, Location Tracking, Communication & Notification System.

At step F20c, the Electronic Identification, Location Tracking, Communication & Notification System automatically queries the Electronic Identification, Location Tracking, Communication & Notification Database to determine the settings configured in 162c for each of the beacons information sent by the App on the customer's device. At step F20d, the Electronic Identification, Location Tracking, Communication & Notification System analyzes the data received from the App and compares it against the retrieved configuration settings (See FIG. 22) for each wireless radio, sound and/or light-based beacon location it received information from. If the customer's device is not considered present at a location based on the analysis of the Electronic Identification, Location Tracking, Communication & Notification System, it will continue to check the next data set received from the App and repeat this step. As a non-limiting example, the signal strength, which in one instance can be measured and calculated on a scale of 0 to 100% was configured to a minimum threshold of 80% (See Block F22c of FIG. 22). This means that unless the customer's device receives a signal from the wireless radio, sound and/or light-based beacons greater than the 80% strength threshold, the customer will not be considered present at a beacon location by the Electronic Identification, Location Tracking, Communication & Notification System. Additionally, a minimum signal strength duration value may be specified for a given location (Block F22d). If so configured, once the App on a customer's electronic system or device reports a signal strength value above the minimum threshold, it must continue to report a signal strength value above that minimum threshold for the configured duration threshold in order to be considered present at that location by the system. Continuing from the non-limiting example above, if this minimum duration threshold is set to 20 seconds, the App must continue to report a signal strength value above the 80% value for a duration of 20 consecutive seconds in order to consider the customer's electronic system or device present at that location by the system.

At step F20e, if the analysis performed in F17d indicates that the customer's device is present at a given location, the system determines if the user is a member of a group or list. If the user is not a member of a group or list, no notifications are sent and the status of that customer's device is updated with the location(s) information that the customer was determined to be at.

At step F20f, if f the customer is determined to be a member of a group or list based on the analysis performed in step F20e, the system next determines what, if any, notifications are configured for the group or list. If notifications are not configured for the group or list the customer is assigned to, no notifications are sent and the status of that customer's device is updated with the location(s) information.

At step F20g, if notifications are configured for the user based on the analysis in F20f, the Electronic Identification, Location Tracking, Communication & Notification Database is updated so the notifications can be queued up. At step F20h, the Electronic Identification, Location Tracking, Communication & Notification Database prompts the Electronic Identification, Location Tracking, Communication & Notification System to send out the configured notifications.

At step F20i, notifications are sent out by the Electronic Identification, Location Tracking, Communication & Notification System via any of the available and configured electronic methods. These methods include but are not limited to Email, SMS, MMS, On Screen and Voice. The notifications are designed to inform specific staff members or departments of the facility or company when specific customers arrive at the location. One non-limiting example of a notification can be a SMS message sent to a Host that one of their VIP customers has arrived at the facility. Another non-limiting example notification is a popup window on a computer screen for the security department when someone tagged on a Watch List arrives at the facility.

FIG. 21 demonstrates another embodiment of how the system determines if a notification is to be delivered, where the notification is to be delivered and how the notification is to be delivered.

At step F21a, the wireless radio, sound and/or light-based beacons installed at various locations are constantly and automatically broadcasting information including, but not limited to, its name, unique identifier (MAC Address, UUID or similar), group/organization, unique number within an organization, location, wireless networks, etc.

At step F21b, the customer's electronic system or device with the Electronic Identification, Location Tracking, Communication & Notification Application "App" downloaded and running receives the broadcasted information from the wireless radio, sound and/or light-based beacons and electronically and automatically transmits the information received, along with additional information including, but not limited to, signal type and strength to the Electronic Identification, Location Tracking, Communication & Notification system. This process can automatically repeat at configurable intervals so that the customer's device is frequently automatically transmitting beacon information to the Electronic Identification, Location Tracking, Communication & Notification System.

At step F21c, the Electronic Identification, Location Tracking, Communication & Notification System queries the Electronic Identification, Location Tracking, Communication & Notification Database to determine the settings configured in F16c for each of the beacon's information sent by the App on the customer's device.

At step F21d, the Electronic Identification, Location Tracking, Communication & Notification System analyzes the data received from the App and compares it against the retrieved configuration settings (See FIG. 22) for each wireless radio, sound and/or light-based beacon location it received information from. If the customer's device is not considered present at a location based on the analysis of the Electronic Identification, Location Tracking, Communication & Notification System, it will continue to check the next data set received from the App and repeat this step. As a non-limiting example, the signal strength, which in one instance can be measured and calculated on a scale of 0 to 100% was configured to a minimum threshold of 80% (See Block F22c of FIG. 22). This means that unless the customer's device receives a signal from the wireless radio, sound and/or light-based beacons greater than the 80% strength threshold, they will not be considered present at a location by the Electronic Identification, Location Tracking, Communication & Notification System. Additionally, a minimum signal strength duration value may be specified for a given location (Block F22d). If so configured, once the App on a customer's electronic system or device reports a signal strength value above the minimum threshold, it must continue to report a signal strength value above that minimum threshold for the configured duration threshold in order to be considered present at that location by the system. Continuing from the non-limiting example above, if this minimum duration threshold is set to 20 seconds, the App must continue to report a signal strength value above the 80% value for a duration of 20 consecutive seconds in order to consider the customer's electronic system or device present at that location by the system.

At step F21e, if the analysis performed in F17d indicates that the customer's device is present at a given location, the system determines if the user is a member of a group or list. If the user is not a member of a group or list, no notifications are sent and the status of that customer's device is updated with that locations information.

At step F21f, if the customer is determined to be a member of a group or list based on the analysis performed in F21e, the system next determines what, if any, notifications are configured for the group or list. If notifications are not configured for the group or list the customer is assigned to, no notifications are sent and the status of that customer's device can be updated with the customer location(s) information.

At step F21g, if notifications are configured for the user based on the analysis in step F21f, the Electronic Identification, Location Tracking, Communication & Notification Database is updated so the notifications can be queued up. At step F21h, the Electronic Identification, Location Tracking, Communication & Notification Database prompts the Electronic Identification, Location Tracking, Communication & Notification System to send out the configured notifications.

At step F21i notifications can be automatically sent out by the Electronic Identification, Location Tracking, Communication & Notification System via any of the available and configured methods. These methods include but are not limited to Email, SMS, MMS, On Screen and Voice. The notifications are designed to inform specific staff members or departments of the facility or company when specific customers arrive at the location. One non-limiting example of a notification can be a SMS message sent to a Host that one of their VIP customers has arrived at the facility. Another non-limiting example notification is a popup window on a computer screen for the security department when someone tagged on a Watch List arrives at the facility.

FIG. 22 demonstrates how a customer's presence at a location can be determined and configured within the Electronic Identification, Location Tracking, Communication & Notification System. This process can also be utilized to edit presence determination configurations already stored in the database.

At step F22a, the Electronic Identification, Location Tracking, Communication & Notification System queries the Electronic Identification, Location Tracking, Communication & Notification Database for a list of available locations. This function can be typically reserved for a system administrator.

At step F22b, the Electronic Identification, Location Tracking, Communication & Notification System displays a listing of available locations to configure. The system administrator can then select the location to configure or edit the configuration of.

At step F22c, once the location is selected, the system administrator may now specify the minimum signal strength threshold for a customer to be considered present at this particular location. This signal strength can be the measure of the strength of a known wireless radio, sound and/or light-based beacons transmitted signal strength as received by the customer's electronic system or device. As a non-limiting example, the signal strength can be measured and calculated on a scale of 0 to 100% where the minimum signal strength threshold is set to 80%. This means that unless the customer's device receives a signal from the wireless radio, sound and/or light-based beacons greater than the 80% strength threshold, they will not be considered present at a location by the Electronic Identification, Location Tracking, & Notification System. The signal strength measurement is intended to approximate the distance between the customers electronic system or device and the wireless radio, sound and/or light-based beacons and can also include strength indicators including, but not limited to, RSSI (relative/received signal strength indicator) values.

At step F22d, once the minimum presence signal strength threshold has been entered, the system administrator has the option of specifying the minimum presence duration for that location. The minimum presence duration is a time value and can be expressed in any known and acceptable time format including, but not limited to, milliseconds, seconds, minutes, hours, etc. As a non-limiting example, the system administrator can configure the value to 20 seconds. In one instance the customer's electronic system or device must report to the Electronic Identification, Location Tracking, Communication & Notification system a signal strength above the minimum threshold specified in F22c for a period of at least 20 consecutive seconds in order to consider the customer's electronic system or device present at that location by the system.

At step F22e, the specific location's presence determination configuration profile can be updated in the Electronic Identification, Location Tracking, Communication & Notification Database.

FIG. 23 demonstrates how a customer is able to order goods and/or services from within or using the Electronic Identification, Location Tracking, Communication & Notification Application running on their electronic system or device.

At step F23a, the customer opens the App on their electronic system or device and selects the order Goods/Services button or link. The App can display all available Goods and/or Service types or categories available for the facility. The customer selects the type/category of good and/or service desired. At step F9b, the App then displays a menu of available goods and/or services for purchase in that type/category to the customer. The customer can select a single good or service, select multiple good and/or services, enter in a free text request, initiate an audio or video session with a facility staff member, or use any other available method to select the goods and/or services desired. At step F23c, the customer's order is electronically transmitted to the Electronic Identification, Location Tracking, Communication & Notification System.

At step F23d, the Electronic Identification, Location Tracking, Communication & Notification System electronically queries the Electronic Identification, Location Tracking, Communication & Notification Database for the notification method associated with the category of good and/or service selected. At step F9e, the Electronic Identification, Location Tracking, Communication & Notification System notifies the appropriate person or department for the category of goods and/or services ordered by the customer of the order and any information provided by the customer.

FIG. 24 demonstrates how a facility is able to deliver goods and/or services ordered by a customer (such as, but not limited to, the ordering process described and shown in FIG. 23) from within the Electronic Identification, Location Tracking, Communication & Notification Application running on the customer's electronic system or device to the current location of the customer at the time of delivery.

At step F24a, a facility staff member or other designated or authorized person uses an electronic system or device to access the Electronic Identification, Location Tracking, Communication & Notification System at the time the good and/or service is ready to be delivered to the customer. At step F24b, the Electronic Identification, Location Tracking, Communication & Notification System queries the Electronic Identification, Location Tracking, Communication & Notification Database for the current location of the customer who placed the order. The current location is determined as in FIGS. 17 and/or 18 and can be constantly and automatically updated within the Electronic Identification, Location Tracking, Communication & Notification System.

At step F24c, the Electronic Identification, Location Tracking, Communication & Notification System then returns the current location of the customer to the Facility staff member's or members' electronic system or device. As an alternative to the customer's current location, the system is programmed to also permit the customer to select another location for the delivery different from their current location (i.e. hotel room where they order from somewhere outside of their room, pool area where they order from somewhere outside of the pool area, etc.)

FIG. 25 demonstrates how a customer is able to opt-out of being rated/monitored from within the Electronic Identification, Location Tracking, Communication & Notification Application on the customer's electronic system or device.

At step F25a, when the Electronic Identification, Location Tracking, Communication & Notification System makes a determination that a customer's electronic system or device is present at a given location as described in FIGS. 17 and/or 18, a notification can be sent to the customer's electronic system or device via the Electronic Identification, Location Tracking, Communication & Notification Application "App" indicating the that their presence has been detected at a given location by the Electronic Identification, Location Tracking, Communication & Notification System. The notification can be made through a variety of methods including but not limited to Email, SMS, MMS, On Screen and Voice.

At step F25b, the customer through the App running on their electronic system or device is presented with or can select a menu item to opt-out of being rated/tracked/monitored by the facility. If the customer does not make an affirmative selection to opt-out of being rated/monitored or makes an affirmative selection to allow rating/monitoring then the Electronic Identification, Location Tracking, Communication & Notification System is electronically notified so that customer rating/monitoring can continue.

At step F25c, if the customer makes an affirmative selection to Opt-Out of being rated/monitored, then the Electronic Identification, Location Tracking, Communication & Notification System is electronically notified of such selection. At step F25d, the Electronic Identification, Location Tracking, Communication & Notification System updates the Electronic Identification, Location Tracking, Communication & Notification Database of the customers' selection in F25b or F25c.

At step F25e, for those customers who made the affirmative selection to Opt-Out of being monitored, the Electronic Identification, Location Tracking, Communication & Notification System queries the Electronic Identification, Location Tracking, Communication & Notification Database to determine if the customer is a member of the Opt-Out Group or List as configured in FIG. 19 for that customer and if so, what the notification settings are for the given customer. At step F25f, for customers determined to be part of the Opt-Out group or list, a notification can be sent via the method configured for the customer and group type in FIG. 19.

The opt out system can also be programmed to function in the opposite as described above. In this alternative embodiment, after receiving the initial notification from the system to the customer that the customer can be electronically tracked by the system, the customer must affirmatively elect to be tracked and if no election is made the system does not track the customer.

The system that performs the above described functions and steps described for the embodiments shown in FIGS. 1-14 can include several components including, but not necessarily limited to:
1. One or more Wireless Radio, Sound and/or Light-based Beacon(s)
2. One or more member/guest electronic computer system or device(s)
3. Access Control & Location Tracking System
4. Access Control & Location Tracking System Database
5. Access Control & Location Tracking Keychain Database
6. A public or private computer network to connect or communicate the beacons and Access Control & Location tracking system and database with each other.

The various components can be in electrical and wireless communication with each other.

The system that performs the above described functions and steps described for the embodiments shown in FIGS. 15-25 can include several components including, but not necessarily limited to, the following:
1. One or more Wireless Radio, Sound and/or Light-based Beacon(s)
2. One or more customer electronic computer system or device(s)
3. Electronic Identification, Location Tracking, Communication & Notification System
4. Electronic Identification, Location Tracking, Communication & Notification Database
5. A public and/or private computer network to connect or communicate the customer's device, beacons and Electronic Identification, Location Tracking, Communication & Notification system and database with each other.

The various components can be in electrical and wireless communication with each other.

The ability to electronically monitor guest and member access to controlled areas will provide significant administrative and financial benefits incident to operators of controlled access locations. Without limitation, these include the following benefits:
1. Provide members with the ability to remotely allow guests entry, rather than necessitating the transfer of a physical object such as a keycard or conventional mechanical key.
2. Provide guests with real-time mapping and navigation in buildings and neighborhoods.
3. Allow members to confirm their guests have arrived and departed.
4. Reduce security costs by allowing increased automation of security systems.
5. Increase safety in controlled access locations by providing real-time data on the presence of unauthorized persons.
6. Provide public safety personnel with access to controlled locations in emergency or other necessary situations.

The ability to electronically identify customers, track customer movements and notify providers of hospitality services of the presence of desired customers will provide significant administrative and financial benefits incident to operators of hospitality venues. Without limitation, these include the following benefits:
1. Provide hospitality service providers the ability to identify a customer and the customer's precise location within their facility.
2. Provide customers with real-time mapping and navigation in buildings and hospitality venues.
3. Provide hospitality service providers the ability to receive notifications when selected customers are present in their facility.
4. Analyze customer levels and behavior so as to tailor or modify service offerings and maximize profitability.

It should be understood that the exemplary embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from their spirit and scope.

All components of the described system and their locations, electronic communication methods between the system components, electronic storage mechanisms, etc. discussed above or shown in the drawings, if any, are merely by way of example and are not considered limiting and other component(s) and their locations, electronic communication methods, electronic storage mechanisms, etc. can be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the system and method has been described and disclosed in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. An electronic system for determining or tracking a current location for an individual within a geographical area, said system comprising:
 an identification and location tracking computer specifically programmed to monitor, track and determine current locations of an individual within a geographical area;
 an identification and location tracking electronic database storing any permissions information for the individual, the electronic database in electronic communication with the tracking computer;
 a plurality of beacons located within the geographical area; each of the plurality of beacons representing a specific location within the geographical area, each specific beacon of the plurality of beacons automatically broadcasting a signal containing unique identification information for the specific beacon; and
 a portable electronic device specifically programmed with a software application for permitting electronic wireless communication between the portable electronic device and one or more of the plurality of beacons, the portable electronic device carried by or on the person of the individual when the individual travels or is present within the geographical area, the software application running on the portable electronic device while the individual travels or is present within the geographical area, while running the software application receives one or more signals broadcasted from one or more specific beacons of the plurality of beacons if in communication range of the portable electronic device;
 wherein when the individual is in a communication range of one or more specific beacons of the plurality of beacons, said portable electronic device receives the unique identification signal broadcasted by each of the one or more specific beacons and said portable electronic device transmits electronic data transmits the electronic data to the tracking computer to allow the tracking computer to determine the current location of the individual within the geographical area.

2. The electronic system of claim 1 wherein electronic information representing the current location of the individual is stored within the tracking electronic database by the tracking computer.

3. The electronic system of claim 1 wherein each beacon of the plurality of beacons is a wireless radio, sound or light-based beacon.

4. The electronic system of claim 1 wherein the tracking computer is programmed to send an electronic notification to a designated person based on permissions information for the individual stored in the tracking electronic database when the tracking computer determines that the individual is present within the geographical area based on the received electronic data.

5. The electronic system of claim 4 wherein the tracking computer is programmed to update the tracking electronic database with information concerning current location of the individual within the geographical area.

6. The electronic system of claim 1 wherein the plurality of beacons are disposed throughout the geographical area such that the current location of the individual within the geographical area can be determined by a greatest signal strength from all of the signal strengths of signals received by the portable electronic device from one or more beacons of the plurality of beacons.

7. The electronic system of claim 6 wherein only beacon signals having signal strengths exceeding a preconfigured signal strength are included by the tracking computer to determine the signal having the greatest signal strength.

8. The electronic system of claim 7 wherein the beacon signal strength has to exceed the preconfigured signal strength for at least a preconfigured duration of time in order to be included by the tracking computer in determining the signal having the greatest signal strength.

9. The electronic system of claim 6 wherein only electronic data for beacon signals having signal strengths exceeding a preconfigured signal strength are transmitted to the tracking computer for use by the tracking computer to determine the current location of the individual within the geographical area.

10. The electronic system of claim 9 wherein the beacon signal strength has to exceed the preconfigured signal strength for at least a preconfigured duration of time in order for electronic data for the beacon to be transmitted to the tracking computer for use by the tracking computer to determine the current location of the individual within the geographical area.

11. The electronic system of claim 1 wherein once the individual is within the geographical area the portable electronic device maintains electronic communication with at least one of the plurality of beacons at all times.

12. The electronic system of claim 1 wherein the tracking computer is programmed to continuously or periodically update the tracking control electronic database with current location information for the individual within the geographical area.

13. The electronic system of claim 1, wherein the geographical area is a facility or place of business.

14. The electronic system of claim 13 wherein the facility or place of business is a casino, restaurant or large venue.

15. The electronic system of claim 1 wherein the portable electronic device directly transmits the electronic data to the tracking computer.

16. The electronic system of claim 1 wherein the portable electronic device indirectly transmits the electronic data to the tracking computer.

17. The electronic system of claim 16 wherein the plurality of beacons in electronic communication with the tracking computer; wherein to indirectly transmit the electronic data to the tracking computer the portable electronic device transmits the electronic data to at least one of the beacons of the plurality of beacons and the at least one beacon transmits the electronic data to the tracking computer.

18. The electronic system of claim 1 wherein the electronic data includes information concerning a signal strength of the unique identification signal received from the specific beacon and a duration of the unique identification signal which is processed by the tracking computer against preconfigured thresholds and if the signal strength and signal duration exceed the preconfigured thresholds the tracking computer deems the individual to be present at or near a preconfigured location of the specific beacon.

19. An electronic method for determining when an individual is present within a geographical area, said method comprising the steps of:
   (a) continuously transmitting unique identification signals by a plurality of beacons located in a geographical area;
   (b) automatically receiving a unique identification signal automatically broadcasted by a specific one of the plurality of beacons by a portable electronic device specifically programmed with a software application for permitting electronic wireless communication between the portable electronic device and the plurality of beacons, wherein the portable electronic device belongs to an individual who carries the portable electronic device or has the portable electronic device on his or her person while the individual is located in the geographical area;
   (c) electronically determining a signal strength for the received unique identification signal and a duration for how long the unique identification signal was received by the portable electronic device;
   (d) wirelessly transmitting electronic data from the portable electronic device to a tracking computer, wherein the electronic data includes information concerning a signal strength of the unique identification signal received from the specific one beacon and a duration of the unique identification signal; and
   (e) electronically determining by the tracking computer whether the signal strength and duration exceed preconfigured signal strength and duration thresholds; wherein where the signal strength and duration exceed the preconfigured thresholds the individual is considered present at or near the location of the specific one beacon
   (b).

20. The electronic method of claim 19 further comprising the step of determining a current location of the individual within the geographical area by the tracking computer system based on the electronic data and a location of the particular beacon within the communication range.

21. The electronic method of claim 20 wherein the location of the particular beacon is selected for determining the current location of the individual where a signal strength between the particular beacon and the portable electronic device is above a predefined signal strength threshold.

22. The electronic method of claim 20 further comprising the step of storing or saving electronic data representing the current location for the individual in a tracking electronic database, the tracking electronic database in communication with the tracking computer system.

23. The electronic method of claim 19 wherein each beacon of said plurality of beacons is a wireless radio, sound or light-based beacon.

24. The electronic method of claim 19 further comprising the step of sending an electronic notification by the tracking computer system to a designated person based on permissions information for the individual stored in a tracking electronic database when the tracking computer determines that the individual is present within the geographical area based on the electronic data received from the portable electronic device.

25. The electronic method of claim 24 wherein the electronic notification informs the designated of a presence of the individual within the geographical area.

26. The electronic method of claim 20 further comprising the step of periodically automatically determining a then current location for the individual within the geographical area and updating the tracking electronic database with any changes in location by the individual within the geographical area.

27. An electronic method for ordering and receiving a product for delivery by an individual located within a geographical area, said method comprising the steps of:
   (a) selecting a product from a list of products displayed on a screen of an electronic portable device by an individual while the individual is located within a geographical area;
   (b) wirelessly forwarding electronic data representing the product selected in step (a) to a tracking computer system; and
   (c) receiving the ordered product by the individual at a current location for the individual within the geographic area determined by (i) wirelessly transmitting electronic data from the portable electronic device to a particular beacon from a plurality of beacons located in the geographical area that is in communication range with the portable electronic device, (ii) transmitting the received electronic data by the particular beacon to the tracking computer system, and (iii) determining the current location by the tracking computer system based on the electronic data and a location of the particular beacon within the geographical area.

28. An electronic method for receiving an order for a product and delivering the ordered product to a current location for an individual within a geographical area, said method comprising the steps of:
   (a) receiving an order for a product by a tracking computer system where the order was originated from an electronic portable device belonging to an individual;
   (b) determining a current location for the individual within a geographical area by (i) wirelessly transmitting electronic data from the portable electronic device to a particular beacon from a plurality of beacons located in the geographical area that is in communication range with the portable electronic device, (ii) transmitting the received electronic data by the particular beacon to the tracking computer system, and (iii) determining the current location by the tracking computer system based on the electronic data and a location of the particular beacon within the geographical area; and
   (c) forwarding information representing the current location for the individual to a person responsible for delivering the product to the individual.

* * * * *